US008066971B2

(12) United States Patent
Torday et al.

(10) Patent No.: US 8,066,971 B2
(45) Date of Patent: Nov. 29, 2011

(54) TARGETING PULMONARY EPITHELIUM USING ADRP

(75) Inventors: John S. Torday, Redondo Beach, CA (US); Virender K. Rehan, Torrance, CA (US)

(73) Assignee: Los Angeles Biomedical Reseach Institute at Harbor UCLA Medical Center, Torrance, CA (US)

( * ) Notice: Subject to any disclaimer, the term of this patent is extended or adjusted under 35 U.S.C. 154(b) by 0 days.

(21) Appl. No.: 11/397,320

(22) Filed: Apr. 3, 2006

(65) Prior Publication Data

US 2006/0286033 A1 Dec. 21, 2006

Related U.S. Application Data

(60) Provisional application No. 60/668,418, filed on Apr. 4, 2005.

(51) Int. Cl.
*A61K 51/00* (2006.01)
*A61K 38/19* (2006.01)
*A61K 38/18* (2006.01)
*A61K 31/7072* (2006.01)
*A61K 31/704* (2006.01)
*A61K 31/4745* (2006.01)
*A61K 31/203* (2006.01)
*A61K 38/21* (2006.01)
*A61K 31/337* (2006.01)

(52) U.S. Cl. ...... 424/1.69; 424/450; 424/85.4; 424/649; 514/120; 514/559; 514/34; 514/283; 514/49; 514/109; 514/449

(58) Field of Classification Search .......................... None
See application file for complete search history.

(56) References Cited

U.S. PATENT DOCUMENTS

| | | | |
|---|---|---|---|
| 5,585,462 | A | 12/1996 | Lomdos et al. |
| 5,739,009 | A * | 4/1998 | Hillman et al. ............. 435/69.1 |
| 5,989,820 | A | 11/1999 | Bandman et al. |
| 6,074,842 | A | 6/2000 | Londos et al. |
| 6,340,577 | B1 | 1/2002 | Hope et al. |
| 6,670,462 | B2 | 12/2003 | Hope et al. |
| 7,049,072 | B2 | 5/2006 | Seshi |
| 2002/0039764 | A1* | 4/2002 | Rosen et al. ................. 435/69.1 |

FOREIGN PATENT DOCUMENTS

WO WO0005173 * 9/2000

OTHER PUBLICATIONS

Quaranta et al (Electrophoresis 2001. 22: 1810-1818).*
Sequence Alignment: Rosen_SEQ90 and ADRP.*
Sequence Alignment: Rosen_SEQ90 and ADRP, (2010).
Adamson et al. "Reciprocal Epithelial: Fibroblast Interactions in the Control of Fetal and Adult Rat Lung Cells in Culture," (1991) *Exp Lung Res.* 17(4): 821-835.
Brasaemle et al. "Perilipin A Increases Triacylglycerol Storage by Decreasing the Rate of Triacylglycerol Hydrolysis," (2000) *J Biol Chem.* 275(49): 38486-38493.
Faridy, "Effect of Distension on Release of Surfactant in Excised Dogs' Lungs," (1976) *Respir Physiol.* 27(1): 99-114.
Gewolb and Torday, "High Glucose Inhibits Maturation of the Fetal Lung In Vitro," (1995) *Lab Invest.* 73(1): 59-63.
Heid et al., "Adipocyte differentiation-related protein is secreted into milk as a constituent of milk lipid globule membrane," (1996) *Biochem J.*, 320 ( Pt 3):1025-1030.
Jobe and Ikegami , "Biology of Surfactant," (2001) *Clin Perinatol.*, 28(3): 655-669.
Londos et al. "Perilipin: unique proteins associated with intracellular neutral lipid droplets in adipocytes and steriodogenic cells," (1995) *Biochem Soc Trans.*, 23(3): 611-615.
McGowan et al., "Expressions of Lipoprotein Receptor and Apolipoprotein E Genes by Perinatal Rat Lipid-Laden Pulmonary Fibroblasts," (2001) *Exp Lung Res.*, 27(1): 47-63.
Miura et al., "Functional Conservation for Lipid Storage Droplet Association among Perilipin, ADRP, and TIP47 (PAT)-related Proteins in Mammals, Drosophila, and Dictyostelium," (2002) *J Biol Chem.* 277(35): 32253-32257.
Nicholas et al., "Surfactant homeostasis in the rat lung during swimming exercise," *J Appl Physiol.* 53(6): 1521-1528), (1982).
Nunez and Torday, "The Developing Rat Lung Fibroblast and Alveolar Type II Cell Activity Recruit Surfactant Phospholipid Substrate," (1995) *J Nutr.* 125(6 Suppl): 1639S-1644S.
Rodriguez et al., "Fetal Androgen Exposure Inhibits Fetal Rat Lung Fibroblast Lipid Uptake and Release," (2001) *Exp Lung Res.* 27(1): 13-24.
Rubin et al., "Arrested Pulmonary Alveolar Cytodifferentiation and Defective Surfactant Synthesis in Mice Missing the Gene for Parathyroid Hormone-Related Protein," (2004) *Dev Dyn.* 230(2): 278-289.
Schultz et al., "Role of adipocyte differentiation-related protein in surfactant phospholipid synthesis by type II cells," (2002) *Am J Physiol Lung Cell Mol Physiol.* 283(2): L288-1296.
Shannon and Hyatt, "Epithelial-Mesenchymal Interactions in the Developing Lung," (2004) *Annu Rev Physiol.*, 66: 625-645.
Torday and Rehan, "Stretch-stimulated surfactant synthesis is coordinated by the paracrine actions of PTHrP and leptin," (2002) *Am J Physiol Lung Cell Mol Physiol.* 283(1):L130-L135. Torday et al., "Metabolism and fate of neutral lipids of fetal lung fiberblast origin," (1995) *Biochim Biophys Acta.*, 1254(2):198-206.
Torday et al., "Paracrine Mediators of Mechanotransduction in Lung Development," (1998) *Am J Med Sci.* 316(3): 205-208.
Torday et al., "Prostaglandin $E_2$ integrates the effects of fluid distension and glucocorticoid on lung maturation," (1998) *Am J Physiol.* 274(1 Pt 1): L106-111.
Torday et al., "Biologic Role of Fetal Lung Fibroblast Triglycerides as Antioxidants," (2001) *Pediatr Res.* 49(6): 843-849.
Weaver et al., "Biogenesis of lamellar bodies, lysosome-related organelles involved in storage and secretion of pulmonary surfactant," (2002) *Semin Cell Dev Biol.* 13(4): 263-270.
Whitsett and Glasser, "Regulation of surfactant protein gene transcription," (1998) *Biochim Biophys Acta.* 1408(2-3): 303-311.
Wright and Clements, "Metabolism and Turnover of Lung Surfactant," (1987) *Am Rev Respir Dis.* 136(2): 426-444.

* cited by examiner

*Primary Examiner* — Scott Long
(74) *Attorney, Agent, or Firm* — Tom Hunter; Weaver Austin Villeneuve & Sampson LLP

(57) ABSTRACT

This invention provides novel compositions and methods for the specific and/or preferential delivery of an effector (e.g. a drug or label) to an epithelial cell (e.g. a pulmonary epithelium). The compositions comprise an adipocyte differentiation-related protein (ADRP) attached to an effector thereby forming a chimeric moiety. The chimeric moiety is preferentially delivered to epithelial cells.

11 Claims, 5 Drawing Sheets

SEQUENCE LISTING

<160> NUMBER OF SEQ ID NOS: 14

<210> SEQ ID NO 1
<211> LENGTH: 4
<212> TYPE: PRT
<213> ORGANISM: Artificial
<220> FEATURE:
<223> OTHER INFORMATION: Peptide linker.

<400> SEQUENCE: 1

Gly Gly Ser Gly
1

<210> SEQ ID NO 2
<211> LENGTH: 5

```
<212> TYPE: PRT
<213> ORGANISM: Artificial
<220> FEATURE:
<223> OTHER INFORMATION: Peptide linker.

<400> SEQUENCE: 2

Gly Gly Gly Gly Ser
1               5

<210> SEQ ID NO 3
<211> LENGTH: 26
<212> TYPE: DNA
<213> ORGANISM: Artificial
<220> FEATURE:
<223> OTHER INFORMATION: Synthetic oligonucleotide primer.

<400> SEQUENCE: 3
ctatggcagc agcagtagtg gatccg                                        26

<210> SEQ ID NO 4
<211> LENGTH: 24
<212> TYPE: DNA
<213> ORGANISM: Artificial
<220> FEATURE:
<223> OTHER INFORMATION: Synthetic oligonucleotide primer.

<400> SEQUENCE: 4
tcatctggcc agcaacatca tgct                                          24

<210> SEQ ID NO 5
<211> LENGTH: 21
<212> TYPE: DNA
<213> ORGANISM: Artificial
<220> FEATURE:
<223> OTHER INFORMATION: Synthetic oligonucleotide primer.

<400> SEQUENCE: 5
ttctagttct tactcagtga g                                             21

<210> SEQ ID NO 6
<211> LENGTH: 21
<212> TYPE: DNA
<213> ORGANISM: Artificial
<220> FEATURE:
<223> OTHER INFORMATION: Synthetic oligonucleotide primer.

<400> SEQUENCE: 6
gctcacgagc tacatcatcc g                                             21

<210> SEQ ID NO 7
<211> LENGTH: 21
<212> TYPE: DNA
<213> ORGANISM: Artificial
<220> FEATURE:
<223> OTHER INFORMATION: Synthetic oligonucleotide primer.

<400> SEQUENCE: 7
ccctttggtc tagtccatca c                                             21

<210> SEQ ID NO 8
<211> LENGTH: 21
<212> TYPE: DNA
<213> ORGANISM: Artificial
<220> FEATURE:
<223> OTHER INFORMATION: Synthetic oligonucleotide primer.

<400> SEQUENCE: 8
```

```
tgtgagatgg cagagaacgg t                                              21
```

<210> SEQ ID NO 9
<211> LENGTH: 21
<212> TYPE: DNA
<213> ORGANISM: Artificial
<220> FEATURE:
<223> OTHER INFORMATION: Synthetic oligonucleotide primer.

<400> SEQUENCE: 9

```
gacctcatgt cctcagccta t                                              21
```

<210> SEQ ID NO 10
<211> LENGTH: 21
<212> TYPE: DNA
<213> ORGANISM: Artificial
<220> FEATURE:
<223> OTHER INFORMATION: Synthetic oligonucleotide primer.

<400> SEQUENCE: 10

```
agacagggat cccagtctaa c                                              21
```

<210> SEQ ID NO 11
<211> LENGTH: 29
<212> TYPE: DNA
<213> ORGANISM: Artificial
<220> FEATURE:
<223> OTHER INFORMATION: Synthetic oligonucleotide primer.

<400> SEQUENCE: 11

```
agcttggatc catggcagca gcagtagta                                      29
```

<210> SEQ ID NO 12
<211> LENGTH: 437
<212> TYPE: PRT
<213> ORGANISM: Homo sapiens

<400> SEQUENCE: 12

Met Ala Ser Val Ala Val Asp Pro Gln Pro Ser Val Val Thr Arg Val
1               5                   10                  15

Val Asn Leu Pro Leu Val Ser Ser Thr Tyr Asp Leu Met Ser Ser Ala
            20                  25                  30

Tyr Leu Ser Thr Lys Asp Gln Tyr Pro Tyr Leu Lys Ser Val Cys Glu
        35                  40                  45

Met Ala Glu Asn Gly Val Lys Thr Ile Thr Ser Val Ala Met Thr Ser
    50                  55                  60

Ala Leu Pro Ile Ile Gln Lys Leu Glu Pro Gln Ile Ala Val Ala Asn
65                  70                  75                  80

Thr Tyr Ala Cys Lys Gly Leu Asp Arg Ile Glu Glu Arg Leu Pro Ile
                85                  90                  95

Leu Asn Gln Pro Ser Thr Gln Ile Val Ala Asn Ala Lys Gly Ala Val
            100                 105                 110

Thr Gly Ala Lys Asp Ala Val Thr Thr Thr Val Thr Gly Ala Lys Asp
        115                 120                 125

Ser Val Ala Ser Thr Ile Thr Gly Val Met Asp Lys Thr Lys Gly Ala
    130                 135                 140

Val Thr Gly Ser Val Glu Lys Thr Lys Ser Val Val Ser Gly Ser Ile
145                 150                 155                 160

Asn Thr Val Leu Gly Ser Arg Met Met Gln Leu Val Ser Ser Gly Val
                165                 170                 175

Glu Asn Ala Leu Thr Lys Ser Glu Leu Leu Val Glu Gln Tyr Leu Pro

|     |     |     |     |     |     |     |     |     |     |     |     |
| --- | --- | --- | --- | --- | --- | --- | --- | --- | --- | --- | --- |
|     |     |     | 180 |     |     |     | 185 |     |     |     | 190 |
| Leu | Thr | Glu | Glu | Leu | Glu | Lys | Glu | Ala | Lys | Lys | Val | Glu | Gly | Phe |
|     |     |     |     | 195 |     |     |     |     | 200 |     |     |     |     | 205 |

| Asp | Leu | Val | Gln | Lys | Pro | Ser | Tyr | Tyr | Val | Arg | Leu | Gly | Ser | Leu | Ser |
| 210 | | | | | 215 | | | | | 220 | | | | | |

| Thr | Lys | Leu | His | Ser | Arg | Ala | Tyr | Gln | Gln | Ala | Leu | Ser | Arg | Val | Lys |
| 225 | | | | | 230 | | | | | 235 | | | | | 240 |

| Glu | Ala | Lys | Gln | Lys | Ser | Gln | Gln | Thr | Ile | Ser | Gln | Leu | His | Ser | Thr |
| | | | | 245 | | | | | 250 | | | | | 255 | |

| Val | His | Leu | Ile | Glu | Phe | Ala | Arg | Lys | Asn | Val | Tyr | Ser | Ala | Asn | Gln |
| | | | 260 | | | | | 265 | | | | | 270 | | |

| Lys | Ile | Gln | Asp | Ala | Gln | Asp | Lys | Leu | Tyr | Leu | Ser | Trp | Val | Glu | Trp |
| | | | 275 | | | | | 280 | | | | | 285 | | |

| Lys | Arg | Ser | Ile | Gly | Tyr | Asp | Asp | Thr | Asp | Glu | Ser | His | Cys | Ala | Glu |
| | | 290 | | | | | 295 | | | | | 300 | | | |

| His | Ile | Glu | Ser | Arg | Thr | Leu | Ala | Ile | Ala | Arg | Asn | Leu | Thr | Gln | Gln |
| 305 | | | | | 310 | | | | | 315 | | | | | 320 |

| Leu | Gln | Thr | Thr | Cys | His | Thr | Leu | Leu | Ser | Asn | Ile | Gln | Gly | Val | Pro |
| | | | | 325 | | | | | 330 | | | | | 335 | |

| Gln | Asn | Ile | Gln | Asp | Gln | Ala | Lys | His | Met | Gly | Val | Met | Ala | Gly | Asp |
| | | | 340 | | | | | 345 | | | | | 350 | | |

| Ile | Tyr | Ser | Val | Phe | Arg | Asn | Ala | Ala | Ser | Phe | Lys | Glu | Val | Ser | Asp |
| | | | 355 | | | | | 360 | | | | | 365 | | |

| Ser | Leu | Leu | Thr | Ser | Ser | Lys | Gly | Gln | Leu | Gln | Lys | Met | Lys | Glu | Ser |
| | | 370 | | | | | 375 | | | | | 380 | | | |

| Leu | Asp | Asp | Val | Met | Asp | Tyr | Leu | Val | Asn | Asn | Thr | Pro | Leu | Asn | Trp |
| 385 | | | | | 390 | | | | | 395 | | | | | 400 |

| Leu | Val | Gly | Pro | Phe | Tyr | Pro | Gln | Leu | Thr | Glu | Ser | Gln | Asn | Ala | Gln |
| | | | | 405 | | | | | 410 | | | | | 415 | |

| Asp | Gln | Gly | Ala | Glu | Met | Asp | Lys | Ser | Ser | Gln | Glu | Thr | Gln | Arg | Ser |
| | | | 420 | | | | | 425 | | | | | 430 | | |

| Glu | His | Lys | Thr | His |
| | | | | 435 |

<210> SEQ ID NO 13
<211> LENGTH: 1907
<212> TYPE: DNA
<213> ORGANISM: Homo sapiens

<400> SEQUENCE: 13

```
gccggagtcg tcttcgggac gcgcctgctc ttcgcctttc gctgcagtcc gtcgatttct    60
ttctccagga agaaaaatgg catccgttgc agttgatcca caaccgagtg tggtgactcg   120
ggtggtcaac ctgcccttgg tgagctccac gtatgacctc atgtcctcag cctatctcag   180
tacaaaggac cagtatccct acctgaagtc tgtgtgtgag atggcagaga acggtgtgaa   240
gaccatcacc tccgtggcca tgaccagtgc tctgcccatc atccagaagc tagagccgca   300
aattgcagtt gccaatacct atgcctgtaa ggggctagac aggattgagg agagactgcc   360
tattctgaat cagccatcaa ctcagattgt tgccaatgcc aaaggcgctg tgactggggc   420
aaaagatgct gtgacgacta ctgtgactgg ggccaaggat tctgtggcca gcacgatcac   480
agggggtgatg gacaagacca agggggcagt gactggcagt gtggagaaga ccaagtctgt   540
ggtcagtggc agcattaaca cagtcttggg gagtcggatg atgcagctcg tgagcagtgg   600
cgtagaaaat gcactcacca aatcagagct gttggtagaa cagtacctcc ctctcactga   660
```

-continued

```
ggaagaacta gaaaagaag caaaaaagt tgaaggattt gatctggttc agaagccaag      720
ttattatgtt agactgggat ccctgtctac caagcttcac tcccgtgcct accagcaggc      780
tctcagcagg gttaaagaag ctaagcaaaa aagccaacag accatttctc agctccattc      840
tactgttcac ctgattgaat ttgccaggaa gaatgtgtat agtgccaatc agaaaattca      900
ggatgctcag ataagctct acctctcatg ggtagagtgg aaaaggagca ttggatatga      960
tgatactgat gagtcccact gtgctgagca cattgagtca cgtactcttg caattgcccg     1020
caacctgact cagcagctcc agaccacgtg ccacaccctc ctgtccaaca tccaaggtgt     1080
accacagaac atccaagatc aagccaagca catgggggtg atggcaggcg acatctactc     1140
agtgttccgc aatgctgcct cctttaaaga agtgtctgac agcctcctca cttctagcaa     1200
ggggcagctg cagaaaatga aggaatcttt agatgacgtg atggattatc ttgttaacaa     1260
cacgcccctc aactggctgg taggtccctt ttatcctcag ctgactgagt ctcagaatgc     1320
tcaggaccaa ggtgcagaga tggacaagag cagccaggag acccagcgat ctgagcataa     1380
aactcattaa acctgcccct atcactagtg catgctgtgg ccagacagat gacaccttt     1440 gttatgttga aattaacttg ctaggcaacc ctaaattggg aagcaagtag ctagtataaa     1500
ggccctcaat tgtagttgtt tccagctgaa ttaagagctt taaagtttct ggcattagca     1560
gatgatttct gttcacctgg taagaaaaga atgataggct tgtcagagcc tatagccaga     1620
actcagaaaa aattcaaatg cacttatgtt ctcattctat ggccattgtg ttgcctctgt     1680
tactgtttgt attgaataaa aacatcttca tgtgggctgg ggtagaaact ggtgtctgct     1740
ctggtgtgat ctgaaaaggc gtcttcactg ctttatctca tgatgcttgc ttgtaaaact     1800
tgattttagt ttttcatttc tcaaatagga atactacctt tgaattcaat aaaattcact     1860
gcaggataaa taaaaaaaaa aaaaaaaaa aaaaaaaaa aaaaaa                     1907
```

<210> SEQ ID NO 14
<211> LENGTH: 437
<212> TYPE: PRT
<213> ORGANISM: Homo sapiens

<400> SEQUENCE: 14

```
Met Ala Ser Val Ala Val Asp Pro Gln Pro Ser Val Val Thr Arg Val
1               5                   10                  15

Val Asn Leu Pro Leu Val Ser Ser Thr Tyr Asp Leu Met Ser Ser Ala
            20                  25                  30

Tyr Leu Ser Thr Lys Asp Gln Tyr Pro Tyr Leu Lys Ser Val Cys Glu
        35                  40                  45

Met Ala Glu Asn Gly Val Lys Thr Ile Thr Ser Val Ala Met Thr Ser
    50                  55                  60

Ala Leu Pro Ile Ile Gln Lys Leu Glu Pro Gln Ile Ala Val Ala Asn
65                  70                  75                  80

Thr Tyr Ala Cys Lys Gly Leu Asp Arg Ile Glu Arg Leu Pro Ile
                85                  90                  95

Leu Asn Gln Pro Ser Thr Gln Ile Val Ala Asn Ala Lys Gly Ala Val
            100                 105                 110

Thr Gly Ala Lys Asp Ala Val Thr Thr Val Thr Gly Ala Lys Asp
        115                 120                 125

Ser Val Ala Ser Thr Ile Thr Gly Val Met Asp Lys Thr Lys Gly Ala
    130                 135                 140

Val Thr Gly Ser Val Glu Lys Thr Lys Ser Val Val Ser Gly Ser Ile
145                 150                 155                 160
```

-continued

```
Asn Thr Val Leu Gly Ser Arg Met Met Gln Leu Val Ser Ser Gly Val
            165                 170                 175

Glu Asn Ala Leu Thr Lys Ser Glu Leu Leu Val Glu Gln Tyr Leu Pro
            180                 185                 190

Leu Thr Glu Glu Glu Leu Glu Lys Glu Ala Lys Lys Val Glu Gly Phe
            195                 200                 205

Asp Leu Val Gln Lys Pro Ser Tyr Tyr Val Arg Leu Gly Ser Leu Ser
    210                 215                 220

Thr Lys Leu His Ser Arg Ala Tyr Gln Gln Ala Leu Ser Arg Val Lys
225                 230                 235                 240

Glu Ala Lys Gln Lys Ser Gln Gln Thr Ile Ser Gln Leu His Ser Thr
            245                 250                 255

Val His Leu Ile Glu Phe Ala Arg Lys Asn Val Tyr Ser Ala Asn Gln
            260                 265                 270

Lys Ile Gln Asp Ala Gln Asp Lys Leu Tyr Leu Ser Trp Val Glu Trp
            275                 280                 285

Lys Arg Ser Ile Gly Tyr Asp Asp Thr Asp Glu Ser His Cys Ala Glu
            290                 295                 300

His Ile Glu Ser Arg Thr Leu Ala Ile Ala Arg Asn Leu Thr Gln Gln
305                 310                 315                 320

Leu Gln Thr Thr Cys His Thr Leu Leu Ser Asn Ile Gln Gly Val Pro
                325                 330                 335

Gln Asn Ile Gln Asp Gln Ala Lys His Met Gly Val Met Ala Gly Asp
            340                 345                 350

Ile Tyr Ser Val Phe Arg Asn Ala Ala Ser Phe Lys Glu Val Ser Asp
            355                 360                 365

Ser Leu Leu Thr Ser Ser Lys Gly Gln Leu Gln Lys Met Lys Glu Ser
    370                 375                 380

Leu Asp Asp Val Met Asp Tyr Leu Val Asn Asn Thr Pro Leu Asn Trp
385                 390                 395                 400

Leu Val Gly Pro Phe Tyr Pro Gln Leu Thr Glu Ser Gln Asn Ala Gln
            405                 410                 415

Asp Gln Gly Ala Glu Met Asp Lys Ser Ser Gln Glu Thr Gln Arg Ser
            420                 425                 430

Glu His Lys Thr His
            435
```

TARGETING PULMONARY EPITHELIUM USING ADRP

CROSS-REFERENCE TO RELATED APPLICATIONS

This application claims benefit of and priority to U.S. Ser. No. 60/668,418, filed on Apr. 4, 2005, which is incorporated herein by reference in its entirety for all purposes.

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention pertains to the field of oncology. In particular, this invention pertains to the discovery that adipocyte differentiation-related protein (ADRP) can be exploited to specifically/preferentially deliver an effector (e.g. a retinoic acid) to a cell comprising the pulmonary epithelium.

BACKGROUND OF THE INVENTION

The pulmonary lipofibroblast is located in the alveolar interstitium where it is distinguished by the presence of large, cytoplasrnic lipid droplets (Heid et al. (1996) *Biochem J.*, 320 (Pt 3):1025-1030; Torday et al. (1995) *Biochim Biophys Acta.*, 1254(2): 198-206). These cells were first described by O'Hare and Sheridan in 1970 (Nicholas et al. *J Appl Physiol.* 53(6): 1521-1528), and their biochemical and structural characteristics were determined during the late 1970s and early 1980s by Brody's group (Heid et al. (1996) Biochem J., 320 (Pt 3):1025-1030; Maksvytis et al. (1984) *J Cell Physiol.*, 118(2):113-123; Maksvytis et al. (1981) *Lab Invest.* 45(3): 248-259; Torday et al. (1995) *Biochim Biophys Acta.*, 1254 (2): 198-206), which named them lipid interstitial cells. McGowan and Torday (McGowan and Torday (1997) *Annu Rev Physiol.* 59: 43-62) have recently critically reviewed the literature on the contributions of these cells to alveolar development and have termed them lipofibroblasts to highlight their fibroblast-like phenotype.

Torday and colleagues (Miura et al. (2002) *J Biol Chem.* 277(35): 32253-32257; Nunez and Torday (1995) *J Nutr.* 125(6 Suppl): 1639S-1644S) have investigated the prenatal ontogeny of the fetal rat lung lipofibroblast, showing a four- to fivefold increase of triacylglycerol in isolated lipofibroblasts, paralleling that in whole lung (Shannon et al. (2001) *Am J Respir Cell Mol Biol.* 24(3):235-244), over the last 4 days of gestation. The triacylglycerol content of fetal rat lung lipofibroblasts is maximal just before the appearance of surfactant phospholipid-containing lamellar bodies in neighboring alveolar type II epithelial (EPII) cells, the site of pulmonary surfactant synthesis (Rodriguez et al. (2001) *Exp Lung Res.* 27(1): 13-24). Torday and coworkers have demonstrated in a coculture system that the triacylglycerols of fibroblast origin are used for surfactant phospholipid synthesis by EPII cells (Rubin et al. (2004) *Dev Dyn.* 230(2): 278-289; Torday et al (1995) *BBA* 1254(2): 198-206) and that the metabolism of these lipids in the culture system is regulated by hormones important for lung maturation (Miura et al. (2002) *J Biol Chem.* 277(35): 32253-32257; Nunez and Torday (1995) *J Nutr.* 125(6 Suppl): 1639S-1644S).

In most mammalian cells, neutral lipids, including those found in pulmonary lipofibroblasts (LIFs), are stored in discrete lipid storage droplets, which are composed of a core of triacylglycerol and cholesterol esters surrounded by a limiting osmophilic boundary (Brasaemle et al. (1997) *J Lipid Res.* 38(11): 2249-2263). Little is known about the proteins that are present at the surface of these lipid storage droplets. The first-described intrinsic lipid droplet-associated proteins were the perilipins, which localize to the periphery of the intracellular neutral lipid storage droplets in adipocytes (Adamson et al. (1991) *Exp Lung Res.* 17(4): 821-835; Gao and Serrero (1999) *J Biol Chem.* 274(24): 16825-16830; Laemmli (1970) *Nature* 227(259): 680-685; O'Hare and Sheridan (1970) *Am J Anat.* 127(2): 181-205) and steroidogenic cells of the adrenal cortex, testes, and ovaries (O'Hare and Sheridan (1970) *Am J Anat.* 127(2): 181-205). Perilipins share sequence homology with adipocyte differentiation-related protein (ADrP), which was first identified as a gene expressed very early in adipocyte differentiation (Heid et al. (1998) *Cell Tissue Res.,* 294(2): 309-321). ADrP, transfected into COS cells, has been shown to play a role in facilitated fatty acid uptake (Frolov et al. (2000) *J Biol Chem.* 275(17): 12769-12780). ADrP mRNA has subsequently been found to be expressed in a wide variety of somatic tissues: heart, brain, spleen, liver, skeletal muscle, kidney, testes, and most pronouncedly in the lung (Brasaemle et al. (1997) *J Lipid Res.* 38(11): 2249-2263; Laemmli (1970) *Nature* 227(259): 680-685). The expression level of ADrP mRNA in adult mouse lung was found to be second only to that in adipose tissue, the tissue that stores the greatest amount of neutral lipid and has the highest expression of ADrP mRNA (Brasaemle et al. (1997) *J Lipid Res.* 38(11): 2249-2263). Schultz et al have determined that lipofibroblasts express ADRP, but that neighboring alveolar type II cells express little if any ADRP. Furthermore, ADRP binds to type II cells, facilitating uptake and incorporation of triglyceride into surfactant phospholipid. ADrP was also identified in human tissues and named adipophilin (Greenberg et al. (1993) *Proc Natl Acad Sci USA.,* 90(24): 12035-12039).

SUMMARY OF THE INVENTION

This invention pertains to novel methods and compositions for directing effectors (e.g. drugs, labels, etc.) to lung epithelium and/or to the nucleus of cells comprising the lung epithelium. The compositions and methods are particularly well suited to direct therapeutic retinoic acid derivatives or other labels or therapeutic moieties directly to the lung epithelium to detect, visualize, and/or to treat lung cancer.

We determined that the ADRP and/or a complex or chimeric moiety comprising ADRP complex binds to the epithelial cell surface and is transported to the nucleus of pulmonary epithelial cells and other cells that participates in the ADRP lipid trafficking mechanism described herein.

This invention thus provides compositions and methods for transporting various effectors to lung tissue. The compositions and methods provided herein are thus useful to treat damaged lung epithelium in acute or chronic lung diseases (e.g., various lung cancers, chronic obstructive pulmonary disease, acute asthma, and the like).

Thus, in certain embodiments, this invention provides a composition comprising an isolated adipocyte differentiation-related protein (ADRP) covalently coupled to or complexed with an effector. In certain embodiments the effector comprises a lipid or liposome, and the lipid or liposome can be empty or can contain or be complexed with a therapeutic agent. In certain embodiments the ADRP is a full length ADRP. In certain embodiments the ADRP is a carboxyl terminal fragment of ADRP of sufficient length to induce transport of the effector (e.g. a lipid or liposome, a cytotoxin, a chelate, etc.) to and/or into an epithelial cell of the lung tissue. In various embodiments lipid or liposome is a neutral lipid or a liposome formed of neutral lipids. In certain embodiments the lipid or liposome is a neutral lipid or a liposome comprising triacylglycerol. In various embodiments the lipid or liposome comprises an agent selected from the group consisting of a retinoid, a prostanoid, an anti-inflammatory agent, a growth factor, a thiazolidinedione, a chemokine, a chemotherapeutic, and the like. In various embodiments the lipid or liposome is a multilamellar liposome or a unilamellar liposome.

In various embodiments this invention also provides a composition comprising an adipocyte differentiation-related protein (ADRP) covalently coupled to, or complexed with, a lipid or liposome, wherein said lipid is complexed with an effector or said liposome contains an effector. In various embodiments the ADRP is a full length ADRP or a fragment (e.g. at least 30, 40, or 50 aa, preferably at least 80, 100, or 150 aa, more preferably at least 200, 250, or 300 aa, and most preferably at least 350 or 400 aa) of an ADRP (e.g., a carboxyl terminal fragment of ADRP of sufficient length to induce transport of the lipid or liposome to or into an epithelial cell of the lung tissue. In certain embodiments the lipid or liposome is a neutral lipid or a liposome formed of neutral lipids that can optionally comprise triacylglycerol. In certain embodiments the lipid or liposome is a multilamellar or a unilamellar liposome. In certain embodiments the effector a label, a cytotoxin, a drug, a prodrug, a cytokine, and the like. When the effector is a cytotoxin, suitable cytotoxins include, but are not limited to a *Diphtheria* toxin, a *Pseudomonas* exotoxin, a ricin, an abrin, and a thymidine kinase. When the effector is a detectable label, suitable detectable labels include, but are not limited to a radioactive label, a spin label, a colorimetric label, a fluorescent label, and a radio-opaque label. In certain embodiments the lagbel is an isotope selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$P, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. In various embodiments the effector comprises an alpha emitter. In various embodiments the effector is a drug selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol.

Also provided is a method of visualizing a tissue comprising ADRP receptors, where the method involves: contacting the tissue with a composition comprising an adipocyte differentiation-related protein (ADRP) covalently coupled to a detectable label (e.g., coupled to or complexed with, a lipid or liposome, wherein said lipid is complexed with a detectable label or the liposome contains a detectable label); and detecting the label in the tissue. In certain embodiments the tissue comprises a small cell carcinoma. In various embodiments, the ADRP is a full length ADRP or an ADRP fragment (e.g., as described above). In certain embodiments the lipid or liposome can include any of the lipids or liposomes described above. In certain embodiments the label is selected from the group consisting of a radioactive label, a spin label, an NMR label, and a radio-opaque label. In certain embodiments the detecting comprises a method selected from the group consisting of an NMR scan, a CAT scan, a PET scan, and an X-ray.

Also provided is a method of inhibiting the growth or proliferation of a tumor cell, where the method involves contacting the tumor cell with a composition comprising an adipocyte differentiation-related protein (ADRP) covalently coupled to, or complexed with an effector comprising a cancer therapeutic (e.g. a lipid or liposome, wherein said lipid is complexed with, or said liposome contains, a cancer therapeutic). In certain embodiments the cancer therapeutic is selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In various embodiments ADRP is a full-length (human) ADRP or an ADRP fragment (e.g., as described above). In certain embodiments the cancer comprises a small cell carcinoma.

This invention also provides a method of preferentially delivering an effector to a cell comprising a pulmonary epithelial cell (e.g., a tumor cell in a mammal), where the method involves providing said effector in a liposome or complexed with a lipid, wherein said lipid or said liposome are complexed with or covalently attached to an adipocyte differentiation-related protein (ADRP); administering said lipid or liposome to said mammal whereby said lipid or liposome is preferentially internalized by said pulmonary epithelial cell. In various embodiments the ADRP includes a full length ADRP or an ADRP fragment (e.g., as described above) and the lipid or liposome comprises a lipid or liposome as described above. In certain embodiments the lipid or liposome comprises an agent selected from the group consisting of a retinoid, a prostanoids, an anti-inflammatories, a growth factor, a thiazolidinediones, a chemokine, and a chemotherapeutic. In certain embodiments the pulmonary epithelia cell comprises a small cell carcinoma. In various embodiments the effector is selected from the group consisting of a label, a cytotoxin, a drug, a prodrug, and a cytokine. @ilce the effector is a cytotoxin selected from the group consisting of a *Diphtheria* toxin, a *Pseudomonas* exotoxin, a ricin, an abrin, and a thymidine kinase. In certain embodiments the effector is a detectable label selected from the group consisting of a radioactive label, a spin label, a colorimetric label, a fluorescent label, and a radio-opaque label. In certain embodiments the effector comprises an isotope selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. In certain embodiments the effector comprises an alpha emitter. In certain embodiments the effector comprises a drug selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol.

Definitions

The terms "polypeptide", "oligopeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The phrase "specifically deliver", as used herein, refers to the preferential association of a molecule, or other moiety, with a cell or tissue bearing a particular target (e.g., receptor, ligand, etc.) or marker as compared to cells or tissues lacking that target target or marker. It is, of course, recognized that a certain degree of non-specific interaction may occur between the moiety and a non-target cell or tissue. Nevertheless, specific delivery, may be distinguished as mediated through specific recognition of the target. Typically specific delivery results in a much stronger association between the delivered moiety and cells bearing the target than between the moiety and cells lacking the target. In certain embodiments specific delivery typically results in greater than 2 fold, preferably greater than 5 fold, more preferably greater than 10 fold and most preferably greater than 100 fold increase in amount of delivered moiety (per unit time) to a cell or tissue bearing the target as compared to a cell or tissue lacking the target or marker.

A "chimeric moiety" or "chimeric structure" refers to a moiety in which two or more moieties (e.g., molecules) that exist separately in their native state are joined together to form a single moiety having the desired functionality of all of its constituent components.

The terms "effector" or "effector component" refers to a moiety that is to be specifically and/or preferentially transported to the target to which the chimeric moiety is directed. The effector typically has a characteristic activity that is desired to be delivered to the target. Effector molecules include, but are not limited to drugs, liposomes, cytotoxins, labels, radionuclides, ligands, antibodies, and the like.

The term "targeting moiety" or "targeting component" refers to a component of a chimeric moiety that specifically and/or preferentially targets a particular cell or cell type. Thus for example, an ADRP targeting moiety refers to a moiety that specifically and/or preferentially binds to or associates with a cell expressing an ADRP receptor. In certain embodiments, the ADRP targeting moiety refers to a moiety (e.g. ADRP, an ADRP fragment, etc.) that participates in the ADRP lipid trafficking mechanism described herein.

The term "residue" as used herein refers to an amino acid that is incorporated into a polypeptide. The amino acid may be a naturally occurring amino acid and, unless otherwise limited, may encompass known analogs of natural amino acids that can function in a similar manner as naturally occurring amino acids.

A "fusion protein" refers to a polypeptide formed by the joining of two or more polypeptides through a peptide bond formed between the amino terminus of one polypeptide and the carboxyl terminus of another polypeptide and/or through a peptide linker. The fusion protein can be formed by the chemical coupling of the constituent polypeptides or it can be expressed as a single polypeptide, e.g., from nucleic acid sequence encoding the single contiguous fusion protein. A single chain fusion protein is a fusion protein having a single contiguous polypeptide backbone.

A "spacer" or "peptide linker" as used herein refers to a peptide that joins the proteins comprising a fusion protein. Generally a spacer has no specific biological activity other than to join the proteins or to preserve some minimum distance or other spatial relationship between them. However, the constituent amino acids of a spacer can be selected to influence some property of the molecule such as the folding, net charge, or hydrophobicity of the molecule.

DETAILED DESCRIPTION

Figure 1:
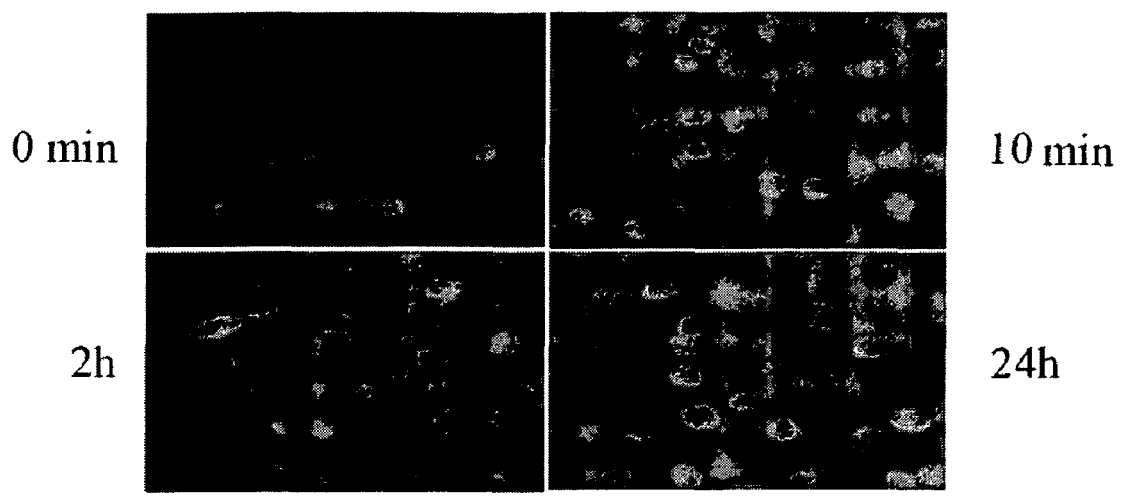
FIG. 1 illustrates the time-course and intracellular localization of the GFP-ADRP lipid complexes in cultured A549 cells. Cultured A549 cells were incubated with GFP-ADRP lipid droplets and examined at 0, 10 min, 2 h, and 24 h by con-focal microscopy. Although there were no visible droplets at the baseline (0 min), there was a rapid uptake and transit of the GFP-ADRP complex to the perinuclear region at 10 min. At 2 h, these complexes were localized to both perinuclear and cytoplasmic compartments, and at 24 h, the GFP-ADRP complexes were more diffusely spread throughout the cytoplasm.

This invention pertains to novel methods and compositions for directing effectors (e.g. drugs, labels, etc.) to lung epithelium and/or to the nucleus of cells comprising the lung epithelium. The compositions and methods are particularly well suited to direct therapeutic retinoic acid derivatives or other labels or therapeutic moieties directly to the lung epithelium to detect, visualize, and/or to treat lung cancer or damaged lung epithelium in acute or chronic lung diseases (e.g., chronic obstructive pulmonary disease, acute asthma, and the like).

Lipids and lipid associated substances such as retinoids are actively taken up from the circulation by lung fibroblasts, which express the Adipocyte Differentiation-Related Protein (ADRP). ADRP is responsible for the uptake and storage of these lipid inclusions, which are typically composed of triglycerides and retinoic acid. The neighboring epithelial cells secrete prostaglandin $E_2$, which causes the secretion of the ADRP lipid complexes by the fibroblasts. We determined that the ADRP complex binds to the epithelial cell surface and is transported to the nucleus, where it stimulates surfactant protein MRNA synthesis, probably due to binding of retinoic acid to the promoter sequence of the surfactant protein gene in the nucleus. Since this targeting mechanism directs retinoids from the circulation to the lung epithelium, it can be exploited to deliver therapeutic retinoic acid derivatives or other moieties directly to the epithelium to treat lung cancer.

In particular, we demonstrated that ADRP complexed to triglyceride/retinoic acid (RA) moves from the circulation to lipofibroblasts, and on to type II cells, where it enters the nucleus to stimulate SP-B MRNA expression. The net result is increased surfactant phospholipid and protein expression. Using green fluorescent protein (GFP)-labeled ADRP lipid droplets to study the transit of lipid droplets through the type II pneumocyte to the nucleus we demonstrated that when H441 cells were incubated with GFP-ADRP Lipid Droplets extracted from Chinese Hamster Ovary cells for 10 minutes and subsequently examined by confocal microscopy. GFP-ADRP localized to the nuclei of the H441 cells. In addition, GFP-ADRP LDs were administered to adult rats intravenously. Uptake of Green Fluorescent Protein-Adipocyte Differentiation Related Protein (GFP-ADRP) lipid droplets in vivo. Was demonstrated.

Without being bound to a particular theory, we believe the trafficking of lipid from the circulation to the epithelial cell nucleus has never been described before. It is a novel route for the exposure of the lung epithelium to substrate or drugs.

Thus, liposomes coated with ADRP, containing all-trans retinoic acid, or other retinoic acid derivatives known to affect lung carcinomas, or various labels, therapeutic or other effectors can be used to deliver the desired effector to the epithelium of the lung. In certain embodiments, the liposomes are into a vehicle (e.g., a pharmaceutically acceptable excipient) and dripped down the airway or injected intravenously.

The methods need not be limited to the use of liposomes. ADRP proteins can be coupled to essentially any moiety that it is desired to preferentially deliver to lung epithelium.

Thus, in certain embodiments, this invention provides for compositions and methods for impairing the growth of tumors. The methods involve providing a chimeric moiety comprising targeting moiety (e.g., ADRP or another moiety that binds an ADRP receptor) attached to an effector. The effector can comprise retinoic acid, and/or other cancer therapeutic (e.g., vinblastine, doxorubicin, a cytotoxin such as *Pseudomonas* exotoxin (PE), *Diphtheria* toxin (DT), ricin, abrin, and the like).

The chimeric moiety is administered to an organism whereby the ADRP component causes preferential and/or specific delivery to the target tissue (e.g. pulmonary epithelia).

The use of chimeric moieties comprising a targeting moiety joined to an effector to target tumor cells has been described. For example, chimeric fusion proteins which include interleukin 4 (IL-4) or transforming growth factor (TGF$\alpha$) fused to *Pseudomonas* exotoxin (PE) or interleukin 2 (IL-2) fused to *Diphtheria* toxin (DT) have been tested for their ability to specifically target and kill cancer cells (Pastan et al. (1992) *Ann. Rev. Biochem.,* 61: 331-354).

In certain embodiments, this invention also provides for compositions and methods for visualizing and/or detecting the presence or absence of target cells (e.g., tumor cells expressing an ADRP receptor). These methods involve providing a chimeric moiety comprising an effector, that is a detectable label attached to a targeting moiety (e.g., ADRP or other moiety that specifically binds an ADRP receptor). The ADRP receptor targeting moiety specifically binds the chimeric moiety to the target cells which are then marked by their association with the detectable label.

In certain embodiments, the effector can be another specific binding moiety such as an antibody, a growth factor, or a ligand. The chimeric structure then acts as a highly specific bifunctional linker. This linker may act to bind and enhance the interaction between cells or cellular components to which the chimeric moiety binds. Thus, for example, where the "targeting" component of the chimeric molecule comprises a polypeptide (e.g., ADRP) that specifically binds to an ADRP receptor and the "effector" component is an antibody or antibody fragment (e.g. an Fv fragment of an antibody), the targeting component specifically binds, e.g., cancerous pulmonary epithelial cells, while the effector component binds receptors (e.g., IL-2 or IL-4 receptors) on the surface of immune cells. The chimeric moiety can thus act to enhance and direct an immune response toward the target cells.

As indicated above, the effector can comprise one or more pharmacological agents (e.g., a drugs) and/or a vehicle comprising a pharmacological agent. This is particularly suitable where it is merely desired to invoke a non-lethal biological response. Thus the moiety that specifically binds to an ADRP receptor may be conjugated to a drug such as retinoic acid, a retinoic acid analogue or derivative, vinblastine, doxirubicin, genistein (a tyrosine kinase inhibitor), an antisense molecule, and other pharmacological agents known to those of skill in the art, thereby specifically targeting the pharmacological agent to cells expressing ADRP receptors.

In certain embodiments, the targeting component can be bound to a vehicle containing the therapeutic composition. Such vehicles include, but are not limited to liposomes, micelles, various synthetic beads, and the like.

One of skill in the art will appreciate that the chimeric moieties/structures of the present invention can include multiple targeting moieties (e.g., ADRPs) bound to a single effector or conversely, multiple effectors bound to a single targeting moiety. In still other embodiment, the chimeric moieties can include both multiple targeting moieties and multiple effector molecules. Thus, for example, this invention provides for "dual targeted" cytotoxic chimeric molecules in which targeting molecule that specifically binds to ADRP is attached to a cytotoxic molecule and another molecule (e.g. an antibody, or another ligand) is attached to the other terminus of the toxin.

The foregoing embodiments are meant to be illustrative and not limiting. Using the embodiments described herein, other suitable ADRP targeting/effector construct ucts will be apparent to one of skill in the art.

I. Indications.

As indicated above, in certain embodiments, the chimeric moieties described herein are used to direct retinoic acid or other retinoids to a target tissue (e.g., pulmonary epithelia). Since retinoids are useful in treating a wide variety of epithelial cell carcinomas-head, neck, esophagus, adrenal, prostate, ovary, testes, pancreas, gut this approach is expected to be useful for all of these life-threatening cancers.

We have also shown that lung fibrosis is due to molecular injury to the epithelium of the lung. Therefore, one can use the chimeric moieties of this invention to treat a wide variety of lung fibrotic diseases including, but not limited to Bronchopulmonary Dysplasia, emphysema, asthma, chronic obstructive lung disease, idiopathic lung fibrosis, and the like.

In addition, there are many chronic degenerative diseases that are characterized by epithelial cell toxicity. These include, but are not limited to pancreatitis, kidney tubular disease, liver fibrosis, reperfusion injury of the vasculature, prostatitis. The chimeric moieties of this invention can be used to treat these conditions as well since all of these tissues utilize the ADRP lipid trafficking mechanism.

II. ADRP Chimeric Moieties.

As explained above, it was a surprising discovery that ADRP can be used as a targeting moiety to specifically direct coupled effectors (e.g., proteins or other moieties) to epithelial tissues, in particular to pulmonary epithelium. In various embodiments this involves the use of chimeric moieties/structures comprising a targeting molecule (e.g., an ADRP) attached to an effector (e.g. a liposome, radionuclide, etc.). The chimeric moieties of this invention specifically target cells bearing ADRP receptors and/or utilizing an ADRP lipid trafficking mechanism (e.g., pulmonary epithelial cells), cells while providing reduced binding to non-target cells.

A) The Targeting Moiety (ADRP).

In various embodiments the targeting component/moiety comprising the chimeric moieties/structures of this invention is adipocyte differentiation-related protein (ADRP) (see, e.g., GenBank Accession No: NP001113). The ADRP can be a full length ADRP or a fragment of ADRP of sufficient length to specifically bind an ADRP receptor. The term "specifically binds", as used herein, when referring to a protein or polypeptide, refers to a binding reaction which is determinative of the presence of the protein or polypeptide in a heterogeneous population of proteins and other biologics. Thus, under designated conditions (e.g. immunoassay conditions in the case of an antibody), the specified ligand (e.g., ADRP) binds to its particular "target" (e.g. an ADRP receptor) and does not bind in a substantial amount to other proteins or receptors present in the sample or to other proteins to which the ADRP or chimeric moiety may come in contact in an organism.

A variety of assay formats can be used to identify ADRP fragments of sufficient length to specifically bind to a ADRP receptor. Such assays are performed in a manner analogous to the use of immunoassays to determine specific binding of an antibody to a particular antigen.

Methods of screening a putative ligand for the ability to bind a particular receptor are well known to those of skill in the art. For example, the receptor can be expressed or over expressed in a host cell. The cell can be contacted with a labeled ligand. After washing to eliminate free ligand, the cell can be screened for the presence of the labeled ligand on the surface and/or internalized. Other screening methods are well known to those of skill in the art.

One of skill in the art will appreciate that analogues or fragments of ADRP bearing will also specifically bind to the ADRP receptor. For example, conservative substitutions of residues (e.g., a serine for an alanine or an aspartic acid for a glutamic acid) comprising native ADRP will provide ADRP analogues that also specifically bind to the ADRP receptor. Thus, the term "ADRP", when used in reference to a targeting molecule, can also include fragments, analogues or peptide mimetics of ADRP that also specifically bind to the ADRP receptor. In preferred embodiment ts, these analogues and/or fragments and/or mimetics will participate in the ADRP lipid trafficking mechanism described herein.

In certain embodiments, to avoid degredation, e.g. if orally delivered, and/or to increase serum half-life, the targeting moiety, and/or the effector can be protected with one or more blocking/protecting groups. Such groups include, but are not limited to polyethylene glycol (PEG), t-butoxycarbonyl (Boc), Fmoc, nicotinyl, OtBu, a benzoyl group, an acetyl (Ac), a carbobenzoxy, methyl, ethyl, a propyl, a butyl, a pentyl a hexyl ester, an N-methyl anthranilyl, and a 3 to 20 carbon alkyl, amide, a 3 to 20 carbon alkyl group, 9-fluoreneacetyl group, 1-fluorenecarboxylic group, 9-fluorenecarboxylic group, 9-fluorenone-1-carboxylic group, benzyloxycarbonyl (is also called carbobenzoxy mentioned above), Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimethyl-2,6-dioxocyclohexylidene)ethyl (Dde), 2,6-dichlorobenzyl (2,6-DiCl—Bzl), 2-chlorobenzyloxycarbonyl (2-Cl—Z), 2-bromobenzyloxycarbonyl (2-Br—Z), benzyloxymethyl (Bom), cyclohexyloxy (cHxO), t-butoxymethyl (Bum), t-butoxy (tBuO), t-Butyl (tBu), trifluoroacetyl (TFA), 4[N-{1-(4,4-dimethyl-2,6-dioxocyclohexylidene)-3-methyldibutyl)-amino}benzyl ester (ODmab), α-allyl ester (OAll), 2-phenylisopropyl ester (2-PhiPr), 1-[4,4-dimethyl-2,6-dioxycyclohex-1-yl-idene)ethyl (Dde), and the like.

In certain embodiments, to improve serum half-life, the targeting moiety and/or the effector can be circularly permuted. Circular permutation is functionally equivalent to taking a straight-chain molecule, fusing the ends (directly or through a linker) to form a circular molecule, and then cutting the circular molecule at a different location to form a new straight chain molecule with different termini (see, e.g., Goldenberg, et al. *J. Mol. Biol.,* 165: 407-413 (1983) and Pan et al. *Gene* 125: 111-114 (1993)). Circular permutation thus has the effect of essentially preserving the sequence and identity of the amino acids of a protein while generating new termini at different locations.

Circular permutation of ADRP provides a means by which the native ADRP protein may be altered to produce new carboxyl and amino termini without diminishing the specificity and binding affinity of the altered first protein relative to its native form. With new termini located away from the active (binding) site, it is possible to incorporate the circularly permuted ADRP into a fusion protein with a reduced, or no diminution, of ADRP binding specificity and/or avidity.

It will be appreciated that while circular permutation is described in terms of linking the two ends of a protein and then cutting the circularized protein these steps are not actually required to create the end product. A protein can be synthesized de novo with the sequence corresponding to a circular permutation of the native protein. Thus, the term "circularly permuted ADRP (cpADRP)" refers to all ADRP proteins having a sequence corresponding to a circular permutation of a no-permuted (e.g., native) ADRP protein regardless of how they are constructed.

Generally, however, a permutation that retains or improves the binding specificity and/or avidity (as compared to the native ADRP) is preferred. If the new termini interrupt a critical region of the native protein, binding specificity and avidity may be lost. Similarly, if linking the original termini destroys ADRP binding specificity and avidity then no circular permutation is suitable. Thus, there are typically two requirements for the creation of an active circularly permuted protein: 1) The termini in the native protein are favorably located so that creation of a linkage does not destroy binding specificity and/or avidity; and 2) There exists an "opening site" where new termini can be formed without disrupting a region critical for protein folding and desired binding activity (see, e.g., Thorton et al. *J. Mol. Biol.*, 167: 443-460 (1983)).

When circularly permuting ADRP, it is desirable to use a linker that preserves the spacing between the termini comparable to the unpermuted or native molecule. Generally linkers are either hetero- or homo-bifunctional molecules that contain two reactive sites that may each form a covalent bond with the carboxyl and the amino terminal amino acids respectively. Suitable linkers are well known to those of skill in the art and include, but are not limited to, straight or branched-chain carbon linkers, heterocyclic carbon linkers, or peptide linkers. The most common and simple example is a peptide linker that typically consists of several amino acids joined through peptide bonds to the termini of the native protein. The linkers can be joined to the terminal amino acids through their side groups (e.g., through a disulfide linkage to cysteine). However, in a preferred embodiment, the linkers are joined to the alpha carbon amino and carboxyl groups of the terminal amino acids.

Functional groups capable of forming covalent bonds with the amino and carboxyl terminal amino acids are well known to those of skill in the art. For example, functional groups capable of binding the terminal amino group include anhydrides, carbodimides, acid chlorides, activated esters and the like. Similarly, functional groups capable of forming covalent linkages with the terminal carboxyl include amines, alcohols, and the like. In a preferred embodiment, the linker will itself be a peptide and will be joined to the protein termini by peptide bonds. A typical linker for circular permutation and/or for joining components of a fusion protein is Gly-Gly-Ser-Gly (SEQ ID NO:1)

One of skill in the art will appreciate that the ADRP can be modified in a variety of ways that do not destroy binding specificity and/or avidity and, in fact, may increase binding properties. Some modifications may be made to facilitate the cloning, expression, or incorporation of the ADRP into a fusion protein. Such modifications are well known to those of skill in the art and include, for example, a methionine added at the amino terminus to provide an initiation site, or additional amino acids placed on either terminus to create conveniently located restriction sites or termination codons.

One of skill will recognize that other modifications may be made. Thus, for example, amino acid substitutions may be made that increase specificity or binding affinity of the circularly permuted protein, etc. Alternatively, non-essential regions of the molecule may be shortened or eliminated entirely. Thus, where there are regions of the molecule that are not themselves involved in the activity of the molecule, they may be eliminated or replaced with shorter segments that merely serve to maintain the correct spatial relationships between the active components of the molecule.

In certain embodiments, the chimeric moiety contains more than one targeting molecule (e.g. a dual-targeted moiety). The chimeric moiety can contain, for example, targeting antibodies directed to tumor markers or other markeers than the ADRP receptor. A number of such antibodies are known and have even been converted to forms suitable for incorporation into fusion proteins. These include anti-erbB2, B3, BR96, OVB3, anti-transferrin, Mik-β1 and PR1 (see Batra et al., *Mol. Cell. Biol.*, 11: 2200-2205 (1991); Batra et al., *Proc. Natl. Acad. Sci. USA*, 89: 5867-5871 (1992); Brinkmann, et al. *Proc. Natl. Acad. Sci. USA*, 88: 8616-8620 (1991); Brinkmann et al., *Proc. Natl. Acad. Sci. USA*, 90: 547-551 (1993); Chaudhary et al., *Proc. Natl. Acad. Sci. USA*, 87: 1066-1070 (1990); Friedman et al., *Cancer Res.* 53: 334-339 (1993); Kreitman et al., *J. Immunol.*, 149: 2810-2815 (1992); Nicholls et al., *J. Biol. Chem.*, 268: 5302-5308 (1993); and Wells, et al., *Cancer Res.*, 52: 6310-6317 (1992), respectively).

B) The Effector.

As described above, the effector component of the chimeric structures of this invention can include any moiety whose activity it is desired to deliver to cells that express ADRP receptors and/or that participate in the ADRP lipid trafficking mechanism described herein. Particularly preferred effector molecules include therapeutic compositions such as liposomes and/or various drugs (e.g., retinoids) cytotoxins such as PE or DT, radionuclides, ligands such as growth factors, antibodies, detectable labels such as fluorescent or radioactive labels, and the like.

1) Retinoic Acid, Analogues and Derivatives.

In certain embodiments, this invention conplates the use of ADRP constructs to specifically and/or preferentially deliver a retinoid to a target tissue. Retinoids are useful in treating a wide variety of epithelial cell carcinomas, including, but not limited to pulmonary, head, neck, esophagus, adrenal, prostate, ovary, testes, pancreas, and gut.

It is noted that ADRP is produced by the connective tissue cells that under lie alveolar cells and the ADRP receptor is found on the alveolar epithelium. The chimeric moieties of this invention are thus particularly well suited to the specific and/or preferential delivery of retinoids (and/or other moieties) to alveolar/pulmonary epithelium.

Retinoic acid, analogues, derivatives, and mimetics are well known to those of skill in the art. Such retinoids include, but are not limited to retinoic acid, ceramide-generating retinoid such as fenretinide (see, e.g., U.S. Pat. No. 6,352,844), 13-cis retinoic acid (see, e.g., U.S. Pat. Nos. 6,794,416, 6,339, 107, 6,177,579. 6,124,485, etc.), 9-cis retinoic acid (see, e.g., U.S. Pat. Nos. 5,932,622, 5,929,057, etc.), 9-cis retinoic acid esters and amides (see, e.g., U.S. Pat. No. 5,837,728), 11-cis retinoic acid (see, e.g., U.S. Pat. No. 5,719,195), all trans retinoic acid (see, e.g., U.S. Pat. Nos. 4,885,311, 4,994,491, 5,124,356, etc.), 9-(Z)-retinoic acid (see, e.g., U.S. Pat. Nos. 5,504,230, 5,424,465, etc.), retinoic acid mimetic anlides (see, e.g., U.S. Pat. No. 6,319,939), ethynylheteroaromatic-acids having retinoic acid-like activity (see, e.g., U.S. Pat. Nos. 4,980,484, 4,927,947, 4,923,884 Ethynylheteroaromatic-acids having retinoic acid-like activity, U.S. Pat. No. 4,739,098, etc.) aromatic retinoic acid analogues (see, e.g., U.S. Pat. No. 4,532,343), N-heterocyclic retinoic acid analogues (see, e.g., U.S. Pat. No. 4,526,7874), naphtenic and heterocyclic retinoic acid analogues (see, e.g., U.S. Pat. No. 518,609), open chain analogues of retinoic acid (see, e.g., U.S. Pat. No. 4,490,414), entaerythritol and monobenzal acetals of retinoic acid esters (see, e.g., U.S. Pat. No. 4,464, 389), naphthenic and heterocyclic retinoic acid analogues (see, e.g., U.S. Pat. No. 4,456,618), azetidinone derivatives of retinoic acid (see, e.g., U.S. Pat. No. 4,456,618), and the like.

The retinoic acid, retinoic acid analogue, derivative, or mimetics can be coupled (e.g., conjugated) to the targeting component (e.g. ADRP) or it can be contained within a liposome or complexed with a lipid that is coupled to the targeting moiety, e.g. as described herein.

2) Other Cancer Therapeutics.

In certain embodiments the methods and compositions of this invention can be used to deliver other cancer therapeutics instead of or in addition to the retinoic acid or retinoic acid analogue/derivative. Such agents include, but are not limited to alkylating agents (e.g., mechlorethamine (Mustargen), cyclophosphamide (Cytoxan, Neosar), ifosfamide (Ifex), phenylalanine mustard; melphalen (Alkeran), chlorambucol (Leukeran), uracil mustard, estramustine (Emcyt), thiotepa (Thioplex), busulfan (Myerlan), lomustine (CeeNU), carmustine (BiCNU, BCNU), streptozocin (Zanosar), dacarbazine (DTIC-Dome), cis-platinum, cisplatin (Platinol, Platinol AQ), carboplatin (Paraplatin), altretamine (Hexalen), etc.), antimetabolites (e.g. methotrexate (Amethopterin, Folex, Mexate, Rheumatrex), 5-fluoruracil (Adrucil, Efudex, Fluoroplex), floxuridine, 5-fluorodeoxyuridine (FUDR), capecitabine (Xeloda), fludarabine: (Fludara), cytosine arabinoside (Cytaribine, Cytosar, ARA-C), 6-mercaptopurine (Purinethol), 6-thioguanine (Thioguanine), gemcitabine (Gemzar), cladribine (Leustatin), deoxycoformycin; pentostatin (Nipent), etc.), antibiotics (e.g. doxorubicin (Adriamycin, Rubex, Doxil, Daunoxome-liposomal preparation), daunorubicin (Daunomycin, Cerubidine), idarubicin (Idamycin), valrubicin (Valstar), mitoxantrone (Novantrone), dactinomycin (Actinomycin D, Cosmegen), mithramycin, plicamycin (Mithracin), mitomycin C (Mutamycin), bleomycin (Blenoxane), procarbazine (Matulane), etc.), mitotic inhibitors (e.g. paclitaxel (Taxol), docetaxel (Taxotere), vinblatine sulfate (Velban, Velsar, VLB), vincristine sulfate (Oncovin, Vincasar PFS, Vincrex), vinorelbine sulfate (Navelbine), etc.), chromatin function inhibitors (e.g., topotecan (Camptosar), irinotecan (Hycamtin), etoposide (VP-16, VePesid, Toposar), teniposide (VM-26, Vumon), etc.), hormones and hormone inhibitors (e.g. diethylstilbesterol (Stilbesterol, Stilphostrol), estradiol, estrogen, esterified estrogens (Estratab, Menest), estramustine (Emcyt), tamoxifen (Nolvadex), toremifene (Fareston) anastrozole (Arimidex), letrozole (Femara), 17-OH-progesterone, medroxyprogesterone, megestrol acetate (Megace), goserelin (Zoladex), leuprolide (Leupron), testosteraone, methyltestosterone, fluoxmesterone (Android-F, Halotestin), flutamide (Eulexin), bicalutamide (Casodex), nilutamide (Nilandron), etc.) INHIBITORS OF SYNTHESIS (e.g., aminoglutethimide (Cytadren), ketoconazole (Nizoral), etc.), immunomodulators (e.g., rituximab (Rituxan), trastuzumab (Herceptin), denileukin diftitox (Ontak), levamisole (Ergamisol), bacillus Calmette-Guerin, BCG (TheraCys, TICE BCG), interferon alpha-2a, alpha 2b (Roferon-A, Intron A), interleukin-2, aldesleukin (ProLeukin), etc.) and other agents such as 1-aspariginase (Elspar, Kidrolase), pegaspasgase (Oncaspar), hydroxyurea (Hydrea, Doxia), leucovorin (Wellcovorin), mitotane (Lysodren), porfimer (Photofrin), tretinoin (Veasnoid), and the like.

3) Cytotoxins.

In certain embodiments, the effector comprises a cytotoxin (e.g. to kill a tumor cell). Suitable cytotoxins include, but are not limited to *Pseudomonas* exotoxins, *Diphtheria* toxins, ricin, abrin, and the like.

*Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity. See Siegall et al., *J. Biol. Chem.* 264: 14256-14261 (1989).

Where the targeting moiety (e.g. ADRP) is fused to PE, one preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as GGGGS (SEQ ID NO:2).

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein. Such modified PE molecules are known to those of skill in the art and include, but are not limited to the incorporation of one or more translocation sequences (e.g., REDL, RDEL, KDEL, etc.) (see, e.g., Chaudhary et al. (1991) *Proc. Natl. Acad. Sci. USA* 87:308-312 and Seetharam et al. (1991) *J. Biol. Chem.* 266: 17376-173810, deletions of amino acids 365-380 of domain Ib, substitution of methionine at amino acid position 280 in place of glycine, and the like (see, e.g., Debinski et al. (1994) *Bioconj. Chem.*, 5: 40).

Like PE, diphtheria toxin (DT) kills cells by ADP-ribosylating elongation factor 2 thereby inhibiting protein synthesis. *Diphtheria* toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) *Science*, 175: 901-903; Uchida et al. (1973) *J. Biol. Chem.*, 248: 3838-3844).

In certain embodiments, the targeting moiety-*Diphtheria* toxin fusion proteins of this invention have the native receptor-binding domain removed by truncation of the *Diphtheria* toxin B chain. Particularly preferred is DT388, a DT in which the carboxyl terminal sequence beginning at residue 389 is removed (see, e.g., Chaudhary, et al. (1991) *Bioch. Biophys. Res. Comm.*, 180: 545-551).

Like the PE chimeric cytotoxins, the DT molecules can be chemically conjugated to the ADRP targeting moiety, but, in a preferred embodiment, the targeting moiety is fused to the *Diphtheria* toxin by recombinant means. The genes encoding protein chains may be cloned in cDNA or in genomic form by any cloning procedure known to those skilled in the art. Methods of cloning genes encoding DT fused to various ligands are also well known to those of skill in the art (see, e.g., Williams et al. (1990) *J. Biol. Chem.* 265: 11885-11889).

The term "*Diphtheria* toxin" (DT) as used herein refers to full length native DT or to a DT that has been modified. Modifications typically include removal of the targeting domain in the B chain and, more specifically, involve truncations of the carboxyl region of the B chain.

4) Detectable Labels.

Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, green fluorescent protein, and the like), radiolabels (e.g., $^{3}H$, $^{25}I$, $^{35}S$, $^{14}C$, or $^{32}P$), enzymes (e.g., horse radish peroxidase, alkaline phosphatase and others commonly used in an ELISA), and calorimetric labels such as colloidal gold or colored glass or plastic (e.g. polystyrene, polypropylene, latex, etc.) beads.

It will be recognized that labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) *Science,* 281: 2013-2016). Similarly, highly fluorescent quantum dots (zinc sulfide-capped cadmium selenide) have been covalently coupled to biomolecules for use in ultrasensitive biological detection (Warren and Nie (1998) *Science,* 281: 2016-2018).

Means of detecting labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and calorimetric labels are detected by simply visualizing the colored label.

5) Ligands.

As explained above, the effector molecule may also comprise a ligand or an antibody. In certain embodiments, the ligands and antibodies are those that bind to surface markers on immune cells. Chimeric molecules utilizing such antibodies as effector molecules act as bifunctional linkers establishing an association between the immune cells bearing binding partner(s) for the ligand or antibody and the target cells expressing the ADRP receptor. Suitable antibodies and growth factors are known to those of skill in the art and include, but are not limited to, IL-2, IL-4, IL-6, IL-7, tumor necrosis factor (TNF), anti-Tac, TGFα, and the like.

6) Other Therapeutic Moieties.

Other suitable effector molecules include various pharmacological agents and/or encapsulation systems containing various pharmacological agents. Thus, the targeting molecule of the chimeric molecule can be attached directly to a drug (e.g. a drug that is to be delivered directly to a tumor). Such drugs are well known to those of skill in the art and include, but are not limited to, doxirubicin, vinblastine, genistein, taxol, antisense molecules, and the like.

In certain embodiments, the effector molecule can comprise an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735, Connor et al., *Pharm. Ther.,* 28: 341-365 (1985)

C. Attachment of the Targeting Moiety to the Effector.

One of skill will appreciate that the targeting moiety (e.g., ADRP) and the effector(s) can be joined together in any order. Thus, for example, the effector can be joined to either the amino or carboxy terminal of the ADRP. The ADRP can may also be joined to an internal region of the effector, or conversely, the effector can be joined to an internal location of the ADRP, as long as the attachment does not interfere with the respective activities of the components.

The targeting moiety and the effector can be attached by any of a number of means well known to those of skill in the art. In certain embodiments, the effector is conjugated, either directly or through a linker (spacer), to the targeting moiety. Where both the effector and the targeting moiety are polypeptides, however, it can be preferable to recombinantly express the chimeric moiety as a fusion protein.

a) Conjugation of the Effector Molecule to the Targeting Molecule.

In certain embodiments, the targeting moiety (e.g., ADP, cpADRP, or anti-ADRPR antibody) is chemically conjugated to the effector molecule (e.g., a liposome, a retinoic acid, a cytotoxin, a label, a ligand, etc.). Means of chemically conjugating molecules are well known to those of skill.

The procedure for attaching an agent to polypeptide or other targeting moiety will vary according to the chemical structure of the agent. Polypeptides typically contain variety of functional groups; e.g., carboxylic acid (COOH) or free amine ($—NH_2$) groups, which are available for reaction with a suitable functional group on an effector molecule to bind the effector thereto.

Alternatively, the targeting molecule and/or effector molecule can be derivatized to expose or attach additional reactive functional groups. The derivatization can involve attachment of any of a number of linker molecules such as those available from Pierce Chemical Company, Rockford Ill.

A "linker", as used herein, typically refers to a molecule that is used to join the targeting moiety to the effector. In various embodiments, the linker is capable of forming covalent bonds to both the targeting moiety and to the effector. Suitable linkers are well known to those of skill in the art and include, but are not limited to, straight or branched-chain carbon linkers, heterocyclic carbon linkers, or peptide linkers. Where the targeting moiety and the effector are polypeptides, the linker(s) can be joined to the constituent amino acids through their side groups (e.g., through a disulfide linkage to cysteine). However, in a certain preferred embodiments, the linkers are be joined to the alpha carbon amino and/or carboxyl groups of the terminal amino acids.

A bifunctional linker having one functional group reactive with a group on a particular agent, and another group reactive with a protein (e.g., ADRP), may be used to form the desired conjugate. Alternatively, derivatization can involve chemical treatment of the targeting moiety. Procedures for generation of, for example, free sulfhydryl groups on polypeptides, such as antibodies or antibody fragments, are known (See U.S. Pat. No. 4,659,839).

Many procedures and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168-

190 (1982); Waldmann (1991) *Science,* 252: 1657; U.S. Pat. Nos. 4,545,985 and 4,894,443, and the like.

In some circumstances, it is desirable to free the effector from the targeting molecule when the chimeric molecule has reached its target site. Therefore, chimeric conjugates comprising linkages which are cleavable in the vicinity of the target site can be used when the effector is to be released at the target site. Cleaving of the linkage to release the agent from the targeting moiety can be prompted by enzymatic activity or conditions to which the conjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

b) Production of Fusion Proteins.

Where the targeting moiety (e.g., ADRP) and/or the effector is relatively short (i.e., less than about 50 amino acids) they may be synthesized using standard chemical peptide synthesis techniques. Where both molecules are relatively short the chimeric moiety can be synthesized as a single contiguous polypeptide. Alternatively the targeting moiety and the effector can be synthesized separately and then fused by condensation of the amino terminus of one molecule with the carboxyl terminus of the other molecule thereby forming a peptide bond. Alternatively, the targeting moiety and the effector can each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield (1963) *Solid-Phase Peptide Synthesis*; pp. 3-284 in *The Peptides: Analysis, Synthesis, Biology. Vol.* 2: *Special Methods in Peptide Synthesis, Part A.*, Merrifield, et al. *J. Am. Chem. Soc.,* 85: 2149-2156; and Stewart et al. (1984) *Solid Phase Peptide Synthesis, 2nd ed.* Pierce Chem. Co., Rockford, Ill.

In certain embodiments, chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. ADRP-effector) of this invention can be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862); the solid support method of U.S. Pat. No. 4,458, 066, and the like.

Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments, DNA encoding fusion proteins of the present invention can be cloned using DNA amplification methods such as polymerase chain reaction (PCR). Thus, for example, the gene for ADRP is PCR amplified, using a sense primer containing the restriction site for NdeI and an anti-sense primer containing the restriction site for HindiHI. This can produce a nucleic acid encoding the mature ADRP sequence and having terminal restriction sites. An effector having "complementary" restrictionsites can similarly be cloned and then ligated to the ADRP targeting moiety and/or to a linker attached to the ADRP targeting moiety. Ligation of the nucleic acid sequences and insertion into a vector produces a vector encoding ADRP joined to the effector.

While the two molecules can be directly joined together, one of skill will appreciate that the molecules can be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins can be expressed in a variety of host cells, including *E. coli*, other bacterial hosts, yeast, and various higher eukaryotic cells such as the COS, CHO and HeLa cells lines and myeloma cell lines. The recombinant protein gene is typically operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.: Deutscher (1990) *Methods in Enzymology Vol.* 182: *Guide to Protein Purification.*, Academic Press, Inc. N.Y., and the like). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the ADRP targeted fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (see, e.g., Debinski et al. (1993) *J. Biol. Chem.*, 268: 14065-14070; Kreitman and Pastan (1993) *Bioconjug. Chem.*, 4: 581-585; and Buchner, et al. (1992) *Anal. Biochem.*, 205: 263-270). Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the ADRP-fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

III. Identification/Validation of Target Cells.

It was a surprising discovery of the present invention that ADRP and/or ADRP-chimeric moieties bind to the epithelial cell surface and are transported to the nucleus. Since the targeting mechanism directs ADRP from the circulation to the lung epithelium, it can be exploited to deliver therapeutic retinoic acid derivatives or other moieties directly to the epithelium, e.g. to image or to treat lung cancer.

Thus, the methods of this invention can be used to target an effector molecule to a variety of cells including, but not limited to a number of epithelial cells (e.g., pulmonary, head, neck, esophagus, adrenal, prostate, ovary, testes, pancreas, gut, and the like). Neoplasias of these tissues are well known to those of skill in the art and include, but are not limited to, cancers of the reproductive system (e.g., testicular, ovarian, cervical), cancers of the gastrointestinal tract (e.g., stomach, small intestine, large intestine, colorectal, etc.), cancers of the head and neck, lung cancers, prostate cancers (e.g., prostate carcinoma), kidney cancers, lung cancers (e.g., mesothelioma), pancreatic cancers, and the like.

One of skill in the art will appreciate that identification and confirmation of effective targeting of a cell or tissue by the constructs of this invention requires only routine screening using well-known methods. Typically this involves providing, e.g. a labeled ADRP (e.g. a radioactive or GFP labeled ADRP). Specific/preferential in vitro and/or in vivo targeting using such a moiety can readily be evaluated, e.g., as described in Example 1.

IV. Pharmaceutical Compositions.

The chimeric moieties of this invention can be useful for parenteral, topical, oral, or local administration, such as by aerosol or transdermally, for prophylactic and/or therapeutic treatment. The chimeric moieties can be formulated into pharmacological compositions (e.g., combination with an appropriate excipient). The pharmacological compositions can be administered in a variety of unit dosage forms depending upon the method of administration. For example, unit dosage forms suitable for oral administration include powder, tablets, pills, capsules and lozenges. It is recognized that the chimeric moieties and pharmaceutical compositions thereof, when administered orally, are typically protected from digestion. This is typically accomplished either by complexing the active component(s) with a composition to render it resistant to acidic and enzymatic hydrolysis or by packaging the composition in an appropriately resistant carrier such as a liposome. Means of protecting proteins and other compositions from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric moietiety dissolved or suspended in a pharmaceutically acceptable carrier, preferably an aqueous carrier. A variety of aqueous carriers can be used, e.g., buffered saline and the like. These solutions are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric moiety in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science,* 15th ed., (1980) Mack Publishing Company, Easton, Pa.

The compositions containing the chimeric moieties and/or a combination of other active agents can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the chimeric moieties described herein is the mitigation or elimination of one or more symptoms of a cancer (e.g., a cancer of an epithelial tissue such as a pulmonary cancer). One preferred application is the treatment of cancer, such as by the use of an ADRP coupled to a retinoic acid or derivative thereof.

It will be appreciated by one of skill in the art that there are some regions that are not heavily vascularized or that are protected by cells joined by tight junctions and/or active transport mechanisms which reduce or prevent the entry of macromolecules present in the blood stream. Thus, for example, systemic administration of therapeutics to treat gliomas, or other brain cancers, is constrained by the blood-brain barrier which resists the entry of macromolecules into the subarachnoid space.

One of skill in the art will appreciate that in these instances, the therapeutic compositions of this invention can be administered directly to the tumor site. Thus, for example, certain tumors can be treated by administering the therapeutic composition directly to the tumor site (e.g., through a surgically implanted catheter). Where the fluid delivery through the catheter is pressurized, small molecules (e.g. the therapeutic molecules of this invention) will typically infiltrate as much as two to three centimeters beyond the tumor margin.

Alternatively, the therapeutic composition can be placed at the target site in a slow release formulation. Such formulations can include, for example, a biocompatible sponge or other inert or resorbable matrix material impregnated with the therapeutic composition, slow dissolving time release capsules or microcapsules, and the like.

Typically the catheter or time release formulation will be placed at the tumor site as part of a surgical procedure. Thus, for example, where major tumor mass is surgically removed, the perfusing catheter or time release formulation can be emplaced at the tumor site as an adjunct therapy. Of course, surgical removal of the tumor mass may be undesired, not required, or impossible, in which case, the delivery of the therapeutic compositions of this invention may comprise the primary therapeutic modality.

VII. Kits.

In certain embodiments, this invention provides for kits for the treatment of tumors or for the detection of certain cells (e.g. cells expressing ADRP receptor s and/or participating in the ADRP lipid trafficking mechanism described herein). Kits typically comprise a chimeric moiety of the present invention (e.g. ADRP-label, ADRP-liposome/retinoic acid, ADRP-ligand, etc.). In addition the kits typically include instructional materials disclosing means of use of the chimeric moiety (e.g. as a therapeutic for a pulmonary cancer, for detection of tumor cells, to augment an immune response, etc.). The kits may also include additional components to facilitate the particular application for which the kit is designed. Thus, for example, where a kit contains a chimeric molecule in which the effector molecule is a detectable label, the kit can additionally contain means of detecting the label (e.g. enzyme substrates for enzymatic labels, filter sets to detect fluorescent labels, appropriate secondary labels such as a sheep anti-mouse-HRP, or the like). The kits can additionally include buffers and other reagents routinely used for the practice of a particular method. Such kits and appropriate contents are well known to those of skill in the art.

EXAMPLES

The following examples are offered to illustrate, but not to limit the claimed invention.

Example 1

ADRP Coordinates Surfactant Phospholipid and Protein Expression

Materials and Methods.

Materials:

A549 cells were obtained from the ATCC, Rockville, Md. Streptomycin, penicillin and RPMI 1640 medium were obtained from Life Technologies (Gaithersburg, Md.). Fetal Bovine Serum was purchased from Hyclone (Logan, Utah). Radiolabeled $^3$H-triolein was purchased from New England Nuclear, Boston, Mass. Time-mated Sprague Dawley rats were purchased from Charles River Breeders, (Holister, Calif.). Animals were treated in accordance with NIH Guidelines, and the protocol was approved by the Los Angeles Biomedical Research Institute. Antibody against Surfactant Protein-B (SP-B) was purchased from Santa Cruz. Biotechnology, Inc (Santa Cruz, Calif.).

Immunoblotting:

Whole lung tissue from pre- and postnatal rats was excised, rinsed in PBS, snap-frozen in liquid $N_2$, and stored at −80° C. until further processing. Frozen lung tissue was homogenized with a Teflon homogenizer in ice-cold hypotonic lysis medium containing 10 mM Tris HCl, pH 7.4, 1 mM EDTA, 10 mM sodium fluoride, 20 μg/ml leupeptin, 1 mM benzamidine, and 100 μM [4-(2-aminoethyl)-benzenesulfonylfluoride]hydrochloride. Protein concentration was measured with a dye binding assay (BioRad) as per the manufacturer's protocol. Aliquots of homogenates (100 μg) were electrophoresed under denaturing SDS-PAGE conditions according to Laemmli (Laemmli (1970) *Nature* 227(259): 680-685) in 10% gels. Immunoblotting was performed by the method of Towbin et al. (Towbin et al. (1979) *Proc Natl Acad Sci USA*. 76(9): 4350-4354). Blots were incubated for 1 h at 25° C. in blocking solution (composed of 5% milk in TBS (10 mM Tris, 0.15 M NaCl, and 0.5% Tween 20 at pH 7.4)) and incubated at 25° C. with a monoclonal antibody (IgG in culture medium diluted 1:10 in blocking solution) against an epitope within the first 25 amino acids of adipophilin, human ADRP (Research Diagnostics). After 2 h, the blots were washed five times (10 min each) in TBS, incubated for 1 h with alkaline-phosphatase-conjugated goat anti-mouse IgG [Jackson ImmunoResearch (1:2,000 in blocking solution)], and finally washed five times (10 min each) with TBS. ADRP protein was detected by reaction of immuno-bound alkaline-phosphatase with 5-bromo-4-chloro-3-indoylphosphate p-toluidine and p-nitro blue tetrazolium chloride as per the manufacturer's instructions (BioRad).

Culture of Fetal Rat Lung Fibroblasts:

Fetal rat lung fibroblasts were prepared and cultured as previously described (Floros et al. (1987) *J Biol Chem.* 262 (28): 13592-13598; Torday et al. (2001) *Pediatr Res.* 49(6): 843-849).

Culture of A549 Cells:

A549 cells were propagated in monolayer in RPMI medium containing 10% fetal bovine serum at 37° C. in an atmosphere of 5% $CO_2$/air.

Preparation of $^3$H-triglyceride-labeled Lipid Droplets.

Fetal lung fibroblast monolayers were incubated with $^3$H-triolein (5:Ci/ml) for 12 h (Torday et al. (1995) *Biochim Biophys Acta.*, 1254(2): 198-206). The cells were gently scraped into PBS and pelleted by centrifugation at 500×g for 5 min at room temperature. ADRP-coated lipid droplets were then isolated from the fibroblasts by differential centrifugation as follows: all pipettes, homogenizers, and tubes were siliconized. Cells were disrupted by incubation in hypotonic lysis medium (as described under Immunoblotting) containing 10% glycerol for 15 min at room temperature followed by 15 strokes in a Teflon-glass homogenizer. The homogenate was centrifuged at 500×g for 5 min. The resulting supernatant (containing lipid droplets) was adjusted to 5-10% sucrose and centrifuged at 50,000×g for 30 min at 4° C., resulting in the lipid droplets forming a floating cake at the top of the centrifuge tube. The lipid cake was removed, resuspended, and homogenized in fresh lysis medium containing glycerol, and again centrifuged at 50,000×g for 30 min at 4° C. The amounts of non-radioactive and radiolabeled triglycerides in the lipid droplet fraction were determined by extraction, chromatography, and quantitation of the triglyceride fraction as previously described (Schultz et al. (2002) *Am. J. Physiol. Lung Cell Mol. Physiol.* 283(2): L288-1296). These washed, $^3$H-labeled lipid droplets were then incubated with cultured A549 cells as described below.

GFP-ADRP Fusion Constructs Expressed in CHO Fibroblasts:

ADRP gene-specific primers were designed from the human ADRP (hADRP) mRNA sequence (GenBank™ accession number BC005127). In conjunction with the Access RT-PCR System (Promega), these primers generate hADRP cDNA from total RNA prepared from the human hepatoma cell line, HuH-7. Total RNA is made using Trizol reagent (Sigma) according to the manufacturer's instructions. The hADRP cDNA is ligated to pGEM-T Easy (Promega) and, from the resultant progeny after transformation, plasmids are screened for the presence of hADRP sequences by restriction endonuclease digestion. Plasmid DNA from positive clones was isolated and the nucleotide sequence of the hADRP cDNA was determined. For the mouse ADRP (mADRP) cDNA, an amplified product was generated using mRNA isolated from mouse L cells and primers (CTA TGG CAG CAG CAG TAG TGG ATC CG (SEQ ID NO:3) and TCA TCT GGC CAG CAA CAT CAT GCT (SEQ ID NO:4)) that were derived from murine sequences generated in the Londos laboratory, NIDDK (GenBank accession number NM007408). The PCR product was inserted into pCRII-TOPO (In vitrogen). A clone containing an mADRP cDNA insert, pCRII/mADRP, was selected by restriction enzyme analysis and the nucleotide sequence of the inserted fragment was determined.

Construction of Plasmids Expressing DNase X, Human and Mouse ADR-P Fused to Fluorescent Proteins:

The hADRP ORF is excised from pLA1 using EcoRI and ligated to EcoRI linearized pEGFPC1 (Clontech) to generate a plasmid termed pLA4 that encodes a GFP-hADRP fusion protein. The same strategy is employed to fuse the hADRP ORF to YFP in plasmid pEYFP-C1 (Clontech). Plasmid pLA5, encoding the N-terminal half of hADRP linked to the C terminus of GFP, was constructed by digesting pLA4 with Bamfi, which removed the 3' terminal region of the hADRP ORF, followed by re-circularization of the digested plasmid. To fuse the C-terminal region of hADRP to GFP, the smaller DNA fragment liberated upon digestion of pLA4 with BamHI is purified and ligated to BamHI linearized pEGFP-C1. This construct is referred to as pLA14. Constructs pLA10, pLA9, and pLA13 encode GFP-hADRP fusion proteins in which premature stop codons are inserted into the coding sequence by site-directed mutagenesis using the Altered Sites II mammalian in vitro mutagenesis system (Promega). This system requires the use of oligonucleotides containing single nucleotide mismatches corresponding to the region of the hADRP ORF to be mutated. Oligonucleotides TTC TAG TTC TTA CTC AGT GAG (SEQ ID NO:5), GCT CAC GAG CTA CAT CAT CCG (SEQ ID NO:6) and CCC TTT GGT CTA GTC CAT CAC (SEQ ID NO:7) are used to generate the GFP-hADRP fusion proteins encoded by pLA10, pLA9, and pLA13, respectively, and premature stop codons are inserted at nucleotide positions 671-673 (pLA10), 593-595 (pLA9), and 503-505 (pLA13) within the hADRP ORF (nucleotides numbered according to the ADRP sequence in BC005 127). N-terminal deletions of the hADRP ORF are created by using oligonucleotides TGT GAG ATG GCA GAG AAC GGT (SEQ ID NO:8) and GAC CTC ATG TCC TCA GCC TAT (SEQ ID NO:9) to amplify regions of the ADRP ORF from internal ATG codons situated at nucleotides 230-232 (pLA11) and 170-172 (pLA12), respectively. In both PCR reactions, the downstream primer used is AGA CAG GGA TCC CAG TCT AAC (SEQ ID NO: 10), which terminates amplification of sequences after the BamHII site is located within the hADRP ORF. The resulting hADRP DNA fragments were ligated into pGEM-T Easy. EcoRI digestion is used to liberate the hADRP DNA fragments from pGEM-T Easy, which are then inserted into EcoRI-linearized pEGFP-C1. To generate pLA17, ligation is performed with hADRP DNA fragments that are liberated upon digestion of pLA12 with EcoRI and BamHI and pLA4 with BamHI and SalI together with pEGFP-C1 linearized with EcoRI and SalI. pLA22 was made by digesting pLA4 with MscI, which removed the region of the hADRP ORF between nucleotides 267 and 476 (inclusive), followed by purification and re-circularization of the digested plasmid using T4 DNA ligase. Construct pLA29 was created by digesting pLA4 with MscI and BamHI, which removes the region of the hADRP ORF between nucleotides 267 and 746 (inclusive). The digested plasmid was purified, treated with Klenow enzyme, and re-circularized using T4 DNA ligase.

For expression of mADRP, a BamHI/SpeI fragment from pCRII/mADRP containing mADRP nucleotide sequences was inserted first into pGEM-1 (Promega) cleaved with HindIII/XbaI along with the oligonucleotide mADRP sequence AGC TTG GAT CCA TGG CAG CAG CAG TAG TA (SEQ ID NO: 11). Because the BamHI/SpeI fragment removes part of the mADRP coding region (the BamHI site lies 15 nucleotides downstream of the ATG initiation codon), oligonucleotide mADRP1 restores these sequences. Inserting this oligonucleotide also abolishes the BamHI site in the mADRP coding region without altering the predicted amino acid sequence and places a novel BamHI site immediately upstream of the ATG codon. The resulting clone is termed pGEM/mADRP. A BamHI fragment from pGEM/mADRP that is introduced into pEGFP-C1 also cleaves with BamHI to give plasmid pGFP-mADRP.

The vector pGFP-DNase X, which directs the synthesis of a GFP-DNase X fusion product, was obtained by initially subcloning a PCR-generated cDNA fragment containing the complete coding region of DNase X into the mammalian expression vector pcDNA3.1 (Invitrogen). The DNase X coding region is fused N-terminal to GFP in pEGFP (Clontech), to give pGFP-DNase X.

Maintenance of Tissue Culture Cells and Generation of Cells Expressing GFP-mADRP HuH-7 and Vero cells were propagated in Dulbecco's modified Eagle's medium supplemented with 10% fetal calf serum, 2 mM L-glutamine, non-essential amino acids, and 100 IU/ml penicillin/streptomycin. To generate cells constitutively expressing GFP-mADRP, CHO cells were transfected with plasmid pGFP-mADRP followed by selection with 800 μg/ml G418 (Clontech). Clones producing GFP-mADRP were selected first by pooling GFP fluorescent cells isolated by fluorescent-activated cell sorting (Beckman) followed by growth of individual colonies. Cloned cell lines were maintained in media containing 500 μg/ml G418.

Preparation of GFP-Labeled Lipid Droplets.

CHO fibroblasts expressing GFP fused to ADRP were incubated with 400 μM oleic acid [coupled to fatty acid-free bovine serum albumin (BSA) at a ratio of 6:1 mol/mol] 24 h at 37° C. in an atmosphere of 5% $CO_2$-air. (Brasaemle et al. (2000) *J Biol Chem.* 275(49): 38486-38493). Lipid droplets were processed as in the case of the $^3$H-triglyceride-labeled lipid droplets (see above). The amount of triglycerides in the lipid droplet fraction was determined by extraction, chromatography, and quantitation of the triglyceride (Torday et al. (1995) *Biochim Biophys Acta.*, 1254(2):198-206).

Incubation of A549 Cells with Lipid Droplets:

Monolayer cultures of A549 cells were incubated with ADRP-LDs labeled with either tritium or GFP as follows: $^3$H-labeled (10,000 dpm/min/20 μg triacylglycerol) ADRP-LDs were isolated from fetal rat lung fibroblasts, as described above. Where indicated, incubations were carried out in the presence of either actinomycin D or cyclohexamide to determine if de novo mRNA or protein synthesis, respectively, was involved in LD processing. Elsewhere, incubations were conducted in the presence of ADRP antibody (rabbit anti-ADRP IgG kindly provided by Dr. Constantine Londos, NIDDK) to determine the specificity of the ADRP effect on LD uptake. At the end of the incubation, the cells were processed for $^3$H-satPC (Floros et al. (1987) *J Biol Chem.* 262(28): 13592-13598), expression of SP-B by RT-PCR and Western Blot (Rehan et al. (2002) *Mol Genet Metab.* 76(1): 46-56), or for confocal microscopy (see below for method).

Determination of Surfactant Phospholipid Synthesis:

The rates of satPC synthesis were determined as previously described (Floros et al. (1987) *J Biol Chem.* 262(28): 13592-13598).

Determination of SP-B Expression:

Western blot and RT-PCR for SP-B were performed as described by Rehan et al. (2002) *Mol Genet Metab.* 76(1): 46-56.

Confocal Microscopy for Documentation of Nuclear Localization:

A549 cells cultured on circular, 1-mm-thick, glass coverslips (Red Label Micro Cover Glasses; Thomas Scientific) were washed three times with PBS, fixed in 3% paraformaldehyde at pH 7.4 for 60 minutes, washed again three times with PBS, and stored in fresh PBS (0-12 hours) at 4° C. until immunostained. The cells were permeabilized with 1% saponin, which was present in all incubations after fixation. Fixed cells were washed, incubated for 60 min in quenching/blocking solution (PBS containing 0.2 M glycine and 1.25 mg of goat IgG/ml), incubated for 18 hours at 4° C. with antibody against ADRP, washed three times with PBS (10 minutes each), incubated for 60 minutes with labeled secondary antibody, and washed again three times with PBS (10 minutes each). Cells were inverted, mounted on coverslips and viewed on a Leica TCS SP II confocal microscope with appropriate filters for fluorescein or rhodamine.

Intravenous Injection of GFP-ADRP Lipid Droplets:

Adult Sprague-Dawley rats were injected intravenously with GFP-ADRP LDs (x, y, z micrograms triglyceride equivalent) and sacrificed with an overdose of pentobarbital 30 minutes post-injection. The lungs were extirpated, perfused x-times with cold PBS to purge them of vascular GFP-ADRP LDs. The lung tissue (rt upper lobe) was snap frozen in liquid nitrogen and kept at −80° C. until further analysis. Lung tissue was processed for GFP using Western Blot technique as described by Rehan et al. (2002) *Mol Genet Metab.* 76(1): 46-56.

Statistical Analyses

Data were analyzed by Analysis of Variance with the Student-Newman-Keuls post-hoc test and t-test as appropriate (Id.).

Results.

Nuclear Translocation of GFP-ADRP in Culture.

Time-Course for A549 Uptake and Localization of GFP-ADRP Complexes:

Upon incubation of A549 cells with GFP-ADRP LDs for 10 minutes (FIG. 1), there was rapid uptake and transit of the complex to the perinuclear region of these cells. After 2 hours the GFP complexes appeared as prominent inclusions in the cytoplasm and perinuclear region of these cells, becoming more diffusely spread over the entire cell by 24 hours.

Figure 2:
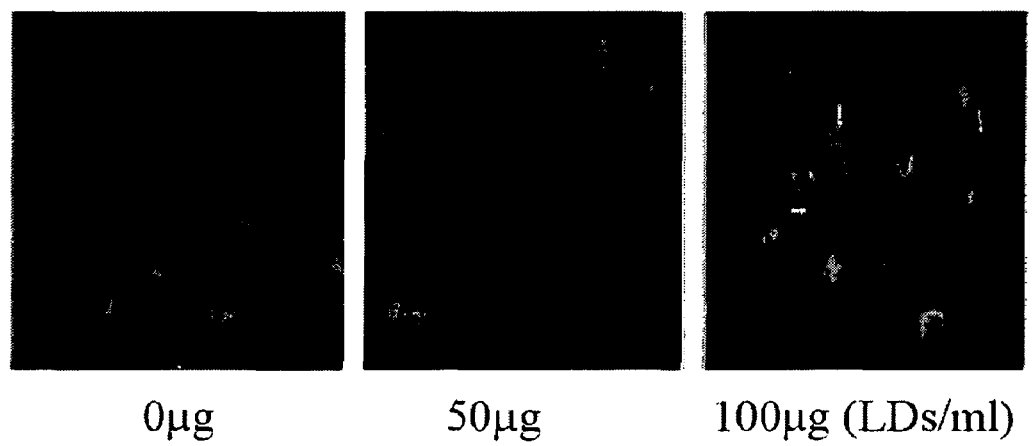
FIG. 2 shows the dose-response and intracellular localization of the GFP-ADRP lipid complexes in cultured A549 cells. Cultured A549 cells were incubated with no added LDs (0 µg/ml, 50 µg/ml or 100 µg/ml medium for 2 h, and then examined by con-focal microscopy. There were no cells showing GFP-ADRP lipid complexes without added LDs, a few with 50 µg/ml LD, and markedly increased GFP-ADRP perinuclear complexes with 100 µg/ml LD (see arrows).

Dose-Dependent A549 Uptake and Localization of GFP-ADRP Complexes:

A549 cells were incubated for 2 h with 0 to 100 :g/ml triglyceride equivalents of GFP-ADRP LD (FIG. 2). There were a few cells containing LDs at the 50 :g/ml dose; at 100 :g/ml there was prominent localization of LDs in the perinuclear (see arrows) and cytoplasmic regions of these cells.

Figure 3:
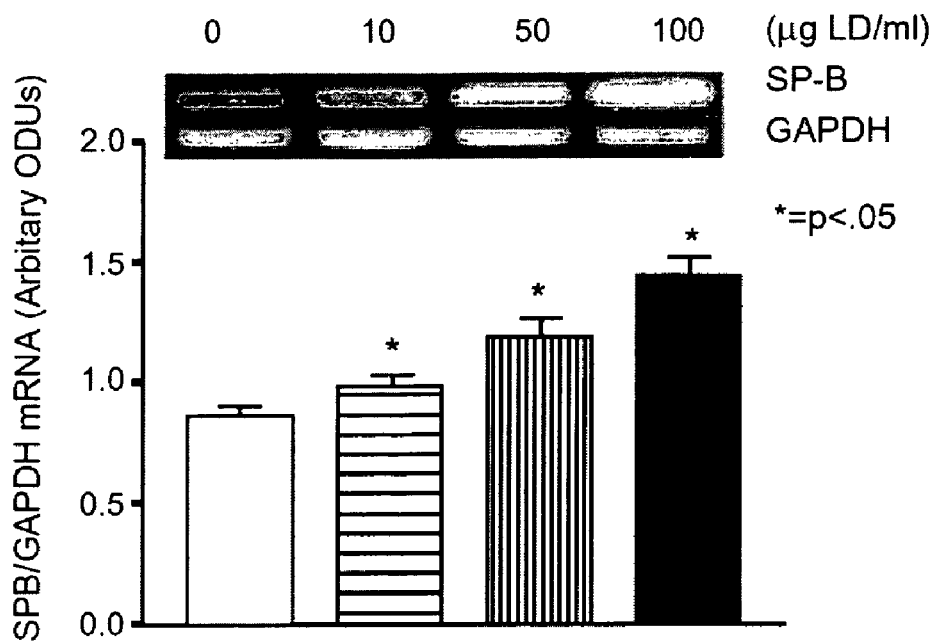
FIG. 3 shows that the uptake of ADRP by A549 cells induces SP-B MRNA expression: Cultured A549 cell monolayers were treated with 0, 10, 50, or 100 µg/ml GFP-ADRP lipid complexes for 24 h, and then SP-B mRNA expression was examined by RT-PCR. Note the step-wise increase in SP-B mRNA expression over the dosage range used, resulting in an 80% increase at the highest LD dose (100 ng/ml) (n=3; *, $p<0.05$ vs controls by Analysis of Variance).
Figure 4:
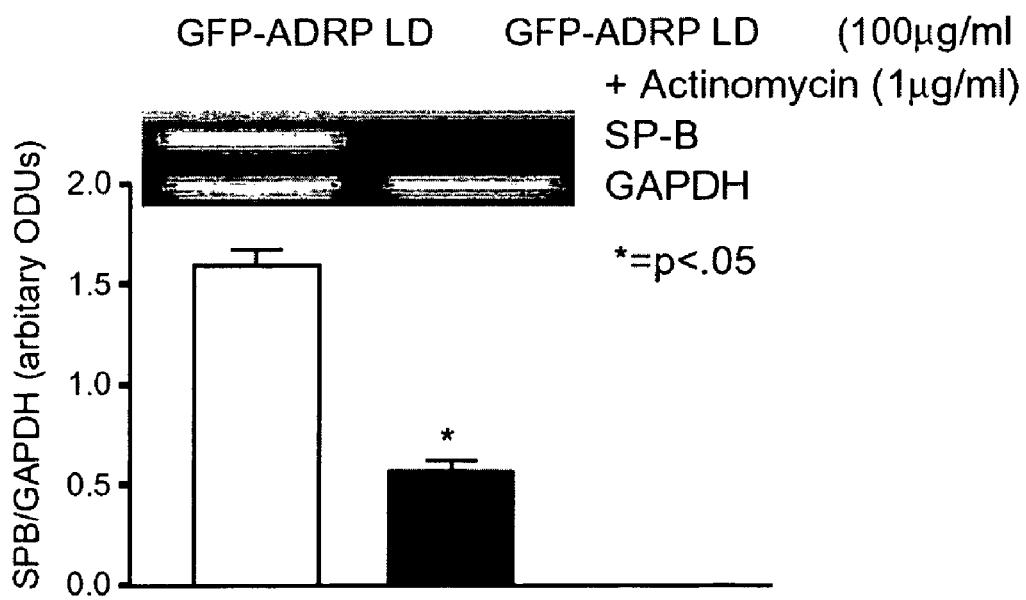
FIG. 4 shows that actinomycin D inhibition of ADRP-induced SP-B miRNA expression. Actinomycin D (1 µg/ml) blocked ADRP induction of SP-B mRNA expression by A549 cells (n=3; *, $p<0.05$ vs without actinomycin by unpaired t test).
Figure 5:
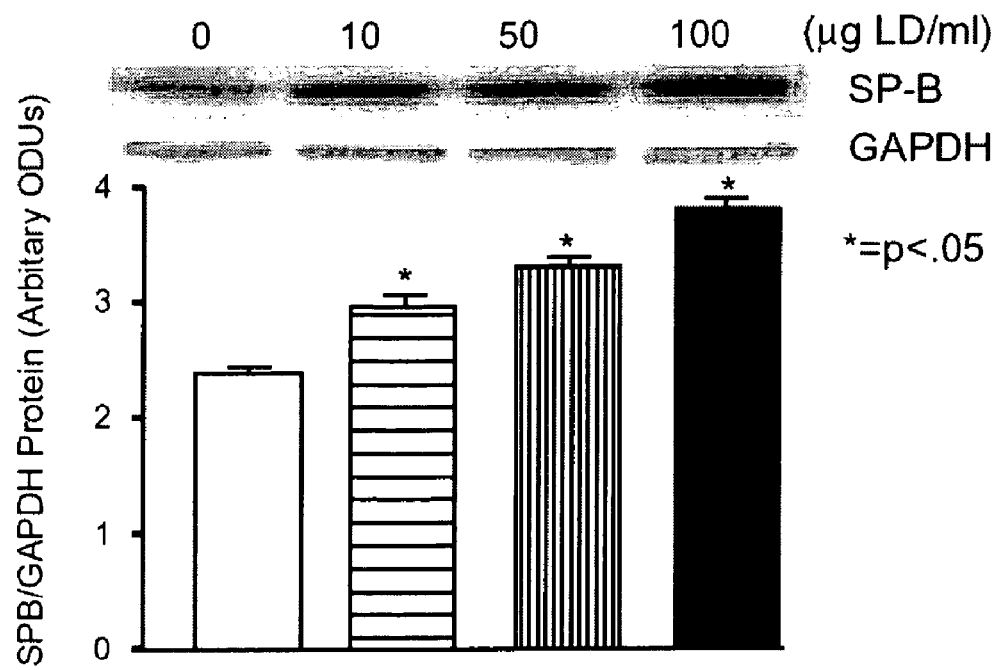
FIG. 5 ADRP increases SP-B protein levels in A549 cells: A549 cell monolayers were treated with 0, 10, 50, or 100 µg/ml GFP-ADRP lipid complexes for 24 h and SP-B levels were subsequently determined by Western blot hybridization. Note the step-wise increase in SP-B protein levels over the dosage range used, resulting in a 50% increase at the highest LD dose (100 ng/ml) (n=3; *, $p<0.05$ vs controls by Analysis of Variance).
Figure 6:
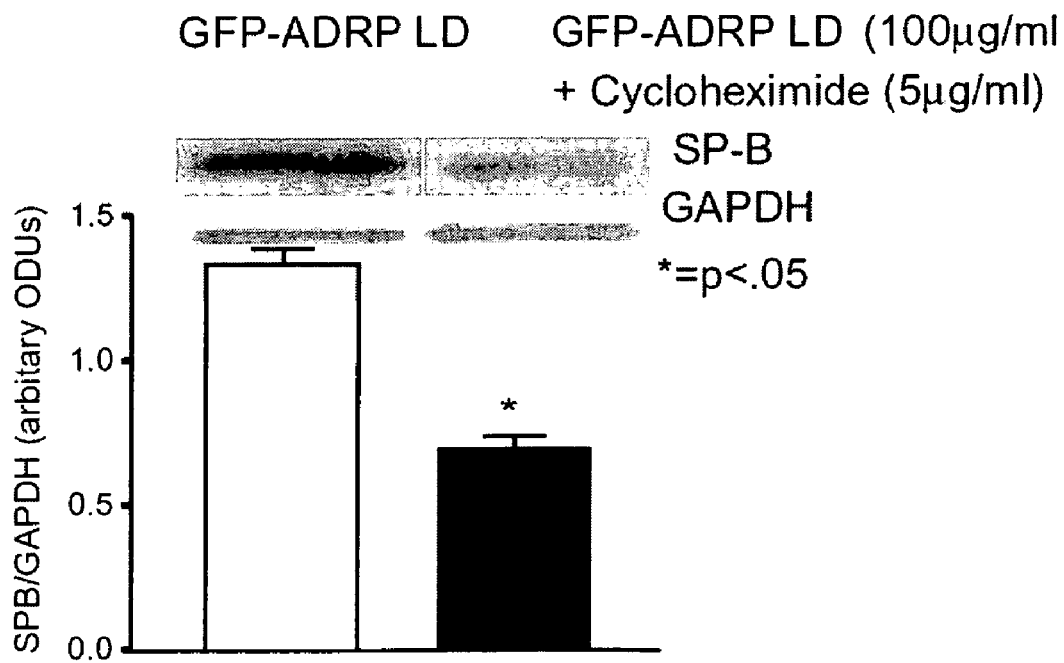
FIG. 6 shows that cycloheximide inhibits ADRP-LD-stimulated SP-B protein increase. Concomitant treatment of A549s incubated with ADRP with cycloheximide (5 :g/ml) inhibited the increase in SP-B protein levels (n=3; *, $p<0.05$ vs without actinomycin by unpaired t test).

Uptake of ADRP by A549 Cells Induces SP-B Expression:

A549 cell monolayer cultures were incubated with graded doses of GFP-ADRP LDs (0, 10, 50, 100 :g/ml) for 24 h, and were subsequently analyzed for SP-B mRNA expression (FIG. 3). Note the step-wise increase in SP-B MRNA expression over the dosage range used, resulting in an 80% increase at the highest LD dose (100 :g/ml). Concomitant incubation with actinomycin D (FIG. 4) blocked the LD induction of SP-B mRNA expression. Using the same study design, we next examined the dose-dependent effect of GFP-ADRP LDs on SP-B protein expression by A549 cell monolayers (FIG. 5). Here again, we observed a dose-dependent increase in SP-B content in response to LD exposure. Co-incubation of these LD-exposed cells with cycloheximide blocked the increase in SP-B protein expression (FIG. 6).

Figure 7:
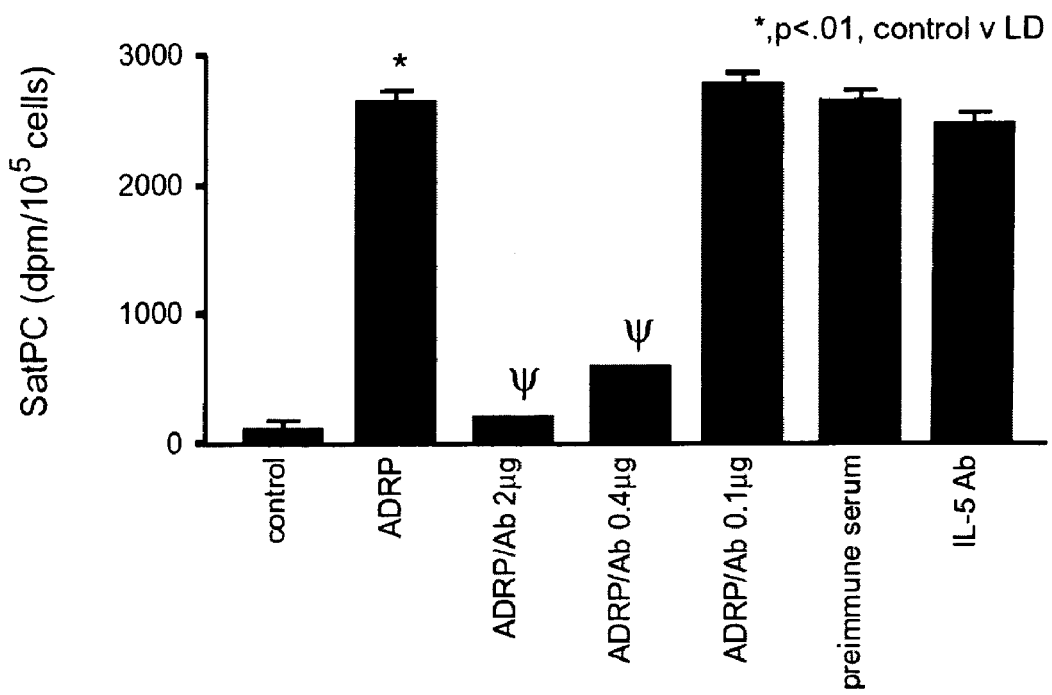
FIG. 7 shows that uptake of ADRP-LDs stimulates surfactant phospholipid synthesis: Incubation of A549 cells with graded doses of ADRP-LDs (100 µg/ml) for 24 h stimulated saturated phosphatidylcholine synthesis 57-fold. Co-incubation of these ADRP-LD-exposed A549 cells with graded doses of ADRP antibody (0.1, 0.4, 2 :g/ml) showed a dose-dependent inhibition of ADRP-LD-induced saturated phosphatidylcholine synthesis (M, $p<0.05$ vs control; ψ, $p<0.001$ vs control). Neither preimmune serum nor a non-specific IL-6 antibody showed the inhibitory effect of ADRP-LD effect on saturated phosphatidylcholine synthesis, indicating the specificity of the ADRP antibody effect.

Uptake of ADRP-LDs Stimulates Surfactant Phospholipid Synthesis:

Incubation of A549 cells with 100 :g/ml of ADRP-LDs for 24 h, which optimally stimulated SP-B expression by these cells, stimulated saturated phosphatidylcholine synthesis 57-fold (FIG. 7). Co-incubation of A549 cells exposed to ADRP-LDs with graded doses of ADRP antibody (0.1, 0.4, 2 :g/ml) showed a dose-dependent inhibition of ADRP-LD-induced saturated phosphatidylcholine synthesis. Neither preimmune serum nor a non-specific IL-6 antibody showed inhibition of the ADRP-LD effect on saturated phosphatidylcholine synthesis, indicating the specificity of the ADRP antibody effect.

Figure 8:
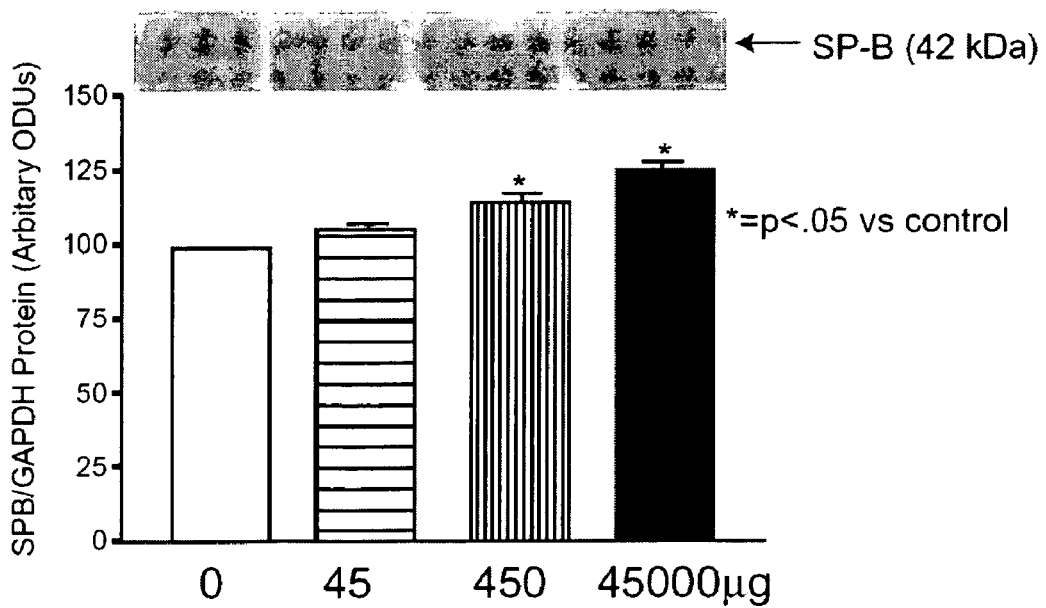
FIG. 8 illustrates uptake of GFP-ADRP LDs in vivo. In vivo administration of graded doses of ADRP-LDs (0, 45, 450, or 4500 :g/kg) to ventilated adult rats resulted in a dose-dependent increase in Surfactant Protein-B expression by the lung 30 minutes after injection. (n=3, *, $p<0.05$ vs control=time 0).

The Functional Effect of ADRP-LDs on SP-B Expression in vivo:

In vivo administration of graded doses of ADRP-LDs (0, 45, 450, or 4500 μg/kg) to ventilated adult rats (FIG. 8) resulted in a dose-dependent increase in SP-B expression in the lung 30 minutes after administration.

Discussion

We have previously shown that cultured fetal rat lung fibroblasts take up and store neutral lipid (Nunez and Torday (1995) *J Nutr.* 125(6 Suppl): 1639S-1644S; Rodriguez et al. (2001) *Exp Lung Res.* 27(1): 13-24; Torday et al. (1995) *Biochim Biophys Acta.,* 1254(2): 198-206; Torday and Rehan (2002) *Am J Physiol Lung Cell Mol Physiol.* 283(1):L130-L135; Torday et al. (1998) *Am J Med Sci.* 316(3): 205-208; Torday et al. (2001) *Pediatr Res.* 49(6): 843-849), whereas cultured fetal rat ATII cells cannot (Torday et al. (1995) *Biochim Biophys Acta.,* 1254(2): 198-206); paradoxically, when these fibroblasts are co-cultured with ATII cells, neutral lipid is actively transferred from fibroblasts to ATII cells and targeted specifically to synthesis of surfactant phospholipids (Id.), suggesting a "docking and trafficking" mechanism. We subsequently found that stretching ATII cells stimulates prostaglandin $E_2$ production (Torday et al. (1998) *Am J Physiol.* 274(1 Pt 1): L106-111), which subsequently stimulates the secretion of neutral lipid by fibroblasts, explaining why fibroblasts release neutral lipid in the presence (but not in the absence) of ATII cells in co-culture (Torday et al. (1995) *Biochim Biophys Acta.,* 1254(2): 198-206). But the mechanism of lipid uptake and targeting remained unexplained. The demonstration of uptake of neutral lipid coated with ADRP in previous experiments provided an explanation for why processing of neutral lipid by fibroblasts is necessary for this mechanism of neutral lipid trafficking (Schultz et al. (2002) *Am J Physiol Lung Cell Mol Physiol.* 283(2): L288-1296). The current set of experiments confirms that ADRP is taken up by ATII cells, and now demonstrates that it is translocated to the perinucleus, coordinately stimulating both surfactant phospholipid and protein synthesis.

The mRNA expression of ADRP, the neutral lipid droplet-associated protein in adult rodent lung, is second only to that in adipose tissue, the tissue that stores the largest amount of neutral lipid and exhibits the highest expression of ADRP mRNA (Brasaemle et al. (2000) *J Biol Chem.* 275(49): 38486-38493). In a previous study, we had found ADRP protein expression in sections of rodent lung tissue localized around lipid droplets. We also reported that ADRP was developmentally expressed in fetal and newborn rat lung, paralleling the accumulation of neutral lipid in lung tissue. Furthermore, the ADRP expression was localized to LIFs, the interstitial lung fibroblasts characterized by cytoplasmic neutral lipid droplets (Londos et al. (1995) *Biochem Soc Trans.*, 23(3): 611-615). In contrast, we found minimal expression of ADRP in primary fetal rat ATII cells, the pneumocytes that lie adjacent to LIFs in the alveolar interstitium (Schultz et al. (2002) *Am J Physiol Lung Cell Mol Physiol.* 283(2): L288-1296) and are the site of pulmonary surfactant synthesis.

The present series of experiments validates the previous study showing ADRP binding and translocation of ADRP-associated LDs to ATIIs (Id.); translocation is now expanded to the A549 cell perinucleus, where ADRP apparently quantitatively stimulates both de novo SP-B expression and surfactant phospholipid synthesis.

During rat lung development LIFs lie in close apposition to ATIIs (Id.), and play a central role in the growth (Weaver et al. (2002) *Semin Cell Dev Biol.* 13(4): 263-270), differentiation (Shannon and Hyatt (2004) *Annu Rev Physiol.*, 66: 625-645) and stability of the epithelial ATII cell phenotype (Shannon et al. (2001) *Am J Respir Cell Mol Biol.* 24(3):235-244). LIFs first appear during the canalicular phase of fetal rat lung development, and triacylglycerol content is maximal just before the appearance of surfactant-containing lamellar bodies in neighboring ATII cells (Torday et al. (1995) *Biochim Biophys Acta.*, 1254(2): 198-206). Despite such apparent evidence for a precursor-product relationship between fibroblast triacylglycerols and ATII cell surfactant phospholipids, there was no empiric evidence for the existence of such a mechanism until we (Id.) demonstrated that triacylglycerols of fibroblast origin are specifically and actively recruited (Schultz et al. (2002) *Am J Physiol Lung Cell Mol Physiol.* 283(2): L288-1296; Torday and Rehan (2002) *Am J Physiol Lung Cell Mol Physiol.* 283(1):L130-L135; Torday et al. (1998) *Am J Med Sci.* 316(3): 205-208; Torday et al. (1998) *Am J Physiol.* 274(1 Pt 1): L106-111) for surfactant phospholipid synthesis by ATII cells in culture.

Initially, we (Torday et al. (1995) *Biochim Biophys Acta.*, 1254(2): 198-206) had demonstrated the accumulation of triacylglycerol by the developing fetal rat lung fibroblast, increasing four- to five fold between embryonic days e18 and e22, with no increase in ATII cell triacylglycerol content. It was later revealed that isolated fetal rat lung fibroblasts, but not ATII cells, actively take up lipid and package it into triacylglycerol-ADRP complexes, providing a mechanistic explanation for the observed accumulation of triacylglycerols by fibroblasts, but not by ATII cells in vivo. To determine the mechanistic significance of these observations (Id.), we 'loaded' the fibroblasts with radiolabeled triacylglycerol and recombined them with ATII cells in organotypic co-culture (Id.) to evaluate transit and metabolism of fibroblast triacylglycerol by ATII cells. There was quantitative transfer of triacylglycerol from fibroblasts to ATII cells, resulting in a threefold increase in the satPC content of the ATII cells. To compare the rate of satPC synthesis from fibroblast triglyceride to that due to circulating substrate, the rate of fibroblast [$^3$H]triacylglycerol incorporation into ATII cell phospholipids was simultaneously compared to the rate of incorporation of extracellular [$^{14}$C]glucose. Both triacylglycerol and glucose were incorporated into ATII cell phospholipids, particularly satPC and phosphatidylglycerol, which are the principal surfactant phospholipids. The rate of triacylglycerol incorporation into satPC and phosphatidylglycerol was 10- to 23-fold higher, respectively, than that of glucose. These data suggested the existence of a specific mechanism for the shuttling of triacylglycerol from the LIF to the ATII cell.

A subsequent series of immunofluorescence experiments (Schultz et al. (2002) *Am J Physiol Lung Cell Mol Physiol.* 283(2): L288-1296) showed that minimal expression of ADRP in ATII cells before co-culture with LIFs was greatly increased along with the transfer of lipid from LIFs after co-culture with LIFs. In addition, anti-ADRP antibodies blocked the transfer of lipid in the co-culture system. Both of these observations suggested an important role of ADRP in the mobilization of intracellular lipid stores from LIFs to ATII cells during fetal lung maturation. In this context, ADRP has also been found on the surface of lipid globules secreted by mammary epithelial cells (Heid et al. (1996) *Biochem J.*, 320 (Pt 3):1025-1030). However, in isolated cultures of LIFs and LIFs co-cultured with ATII cells, we found no evidence of secreted ADRP, by either Western blotting or radiolabeled protein techniques. During the time of increased triacylglycerol accumulation in the developing lung, cytoplasmic projections are present between LIFs and ATII cells (Adamson et al. (1991) *Exp Lung Res.* 17(4): 821-835), giving rise to the possibility that the lipid transfer may occur via these connections.

In the present series of experiments, we have used a GFP-ADRP fusion construct to determine if ADRP is taken up by ATII cells and what its intracellular fate is. We have discovered that ADRP-LD complexes traverse the plasma membrane and initially localize around the nucleus, subsequently migrating to the cytoplasm. This process is associated with up-regulation of both surfactant protein and phospholipid synthesis, and can be blocked by inhibitors of RNA and protein synthesis. Taken together, these data, for the first time, provide a cell/molecular mechanism for the long-recognized (Jobe and Ikegami (2001) *Clin Perinatol.*, 28(3): 655-669) coordinate regulation of the phospholipid and protein moieties of the surfactant. Of equal, if not greater importance is the fact that ADRP is regulated by Parathyroid Hormone-related Protein (PTHrP) (Torday and Rehan (2002) *Am J Physiol Lung Cell Mol Physiol.* 283(1):L130-L135), linking the regulation of surfactant protein and phospholipid synthesis to stretch, since PTHrP is a stretch-regulated gene expressed by the ATII cell (Torday and Rehan (2002) *Am J Physiol Lung Cell Mol Physiol.* 283(1):L130-L135; Torday et al. (1998) *Am J Med Sci.* 316(3): 205-208).

McGowan et al. (McGowan et al. (2001) *Exp Lung Res.*, 27(1): 47-63) have evaluated the roles of lipoprotein receptors and Apolipoprotein E (ApoE) in the accumulation of circulating lipoproteins by LIFs. Because they found no correlation between developmental age of the LIFs and their lipoprotein receptors or ApoE expression, they concluded that such changes must, alternatively, be due to the amounts of lipoprotein in circulation. The concentration of triglyceride in fetal rat circulation is 40-fold lower than in fetal rat lung LIFs (Torday et al. (1995) *Biochim Biophys Acta.*, 1254(2): 198-206), and although it increases in the postnatal period, it does not correlate with the pattern of triglyceride content in developing LEFs (Id.). Furthermore, we have shown that both endocrine hormones (Nunez and Torday (1995) *J Nutr.* 125(6 Suppl): 1639S-1644S; Rodriguez et al. (2001) *Exp Lung Res.* 27(1): 13-24; Torday et al. (2001) *Pediatr Res.* 49(6): 843-849) and paracrine factors (Torday and Rehan (2002) *Am J Physiol Lung Cell Mol Physiol.* 283(1):L130-L135; Torday et al. (1998) *Am J Med Sci.* 316(3): 205-208) have direct effects on the rate of LIF triglyceride accumulation, indicating that this process is regulated at the cellular level. In contrast to the dissociation of circulating triglyceride levels during the perinatal period from the ontogeny of triglycerides in LIFs, the pattern of LIF expression of ADRP (Schultz et al. (2002) *Am J Physiol Lung Cell Mol Physiol.* 283(2): L288-1296) is consistent with its hypothesized role in LIF triglyceride accumulation.

Lung surfactant production is widely recognized to be under both hormonal (Mendelson (2000) Pp. 141-159 In: *Endocrinology of the Lung. Humana Press*, Totawa, N.J.) and paracrine regulation (Wolins et al. (2001) *J Biol Chem.* 276 (7): 5101-5118). In the LIF-ATII cell co-culture system, dexamethasone was shown to selectively stimulate LIF triacylglycerol incorporation into ATII cell satPC (Nunez and Torday (1995) *J Nutr.* 125(6 Suppl): 1639S-1644S), indicating the existence of a specific mechanism for triacylglycerol mobilization from the fibroblast to the ATII cells that is hormonally regulated. Studies indicate that the increase in ADRP expression by ATII cells after co-culture with LIFs is blocked by incubation with an antagonist of PTHrP (37), a necessary determinant of lung maturation (Rubin et al. (2004) *Dev Dyn.* 230(2): 278-289). That finding suggests that endogenous PTHrP promotes the lipid transfer between LIFs and ATII cells and the change in ADRP expression in ATII cells that accompanies this transfer.

PTHrP is a stretch-regulated product of the ATII cell which signals the up-regulation of both ADRP (Torday and Rehan (2002) *Am J Physiol Lung Cell Mol Physiol.* 283(1):L130-L135) and leptin (Id.) by LIFs. When these previous observations are combined with the present results showing coordinate surfactant protein and phospholipid expression by ATIIs through the action of ADRP-LDs, it provides the first integrated cell-molecular mechanism for the 'on-demand' stretch-regulated surfactant production, initially demonstrated by Faridy (Faridy (1976) *Respir Physiol.* 27(1): 99-114), and then by others (Nicholas et al. *J Appl Physiol.* 53(6): 1521-1528).

The possible involvement of ADRP, a protein intrinsic to intracellular lipid droplets, in the transfer of triacylglycerol from LIFs to ATII cells suggests a novel mechanism for the trafficking of neutral lipids between these two cell-types. No ADRP protein was found in the culture medium of LIFs alone or in co-cultures with ATII cells. This observation, in combination with the close apposition (Gewolb and Torday (1995) *Lab Invest.* 73(1): 59-63) and cellular projections between LIFs and ATII cells (Adamson et al. (1991) *Exp Lung Res.* 17(4): 821-835), would suggest that the lipid shuttling mechanism between these two cell-types is not the same as that for circulating lipoproteins, which involves secretion and possible uptake of whole lipid particles. In this context, TIP47, a recently described protein highly homologous to ADRP (Wright and Clements (1987) *Am Rev Respir Dis.* 136(2): 426-444), has been reported to bind to the cytoplasmic domain of mannose 6-phosphate receptors and mediate receptor uptake and targeting to the lysosomal compartment. This pathway is very similar to the processing of lipids and proteins for surfactant phospholipid synthesis and storage within lamellar bodies, which are modified lysosomes (Whitsett and Glasser (1998) *Biochim Biophys Acta.* 1408(2-3): 303-311). Interestingly, a separate study has also demonstrated that TIP47 targets to lipid storage droplets (Miura et al. (2002) *J Biol Chem.* 277(35): 32253-32257). Furthermore, we have previously shown that LIFs secrete lipid and that prostaglandin $E_2$ of ATII cell origin is an agonist for such secretion (Torday et al. (1998) *Am J Physiol.* 274(1 Pt 1): L106-111).

Figure 9:
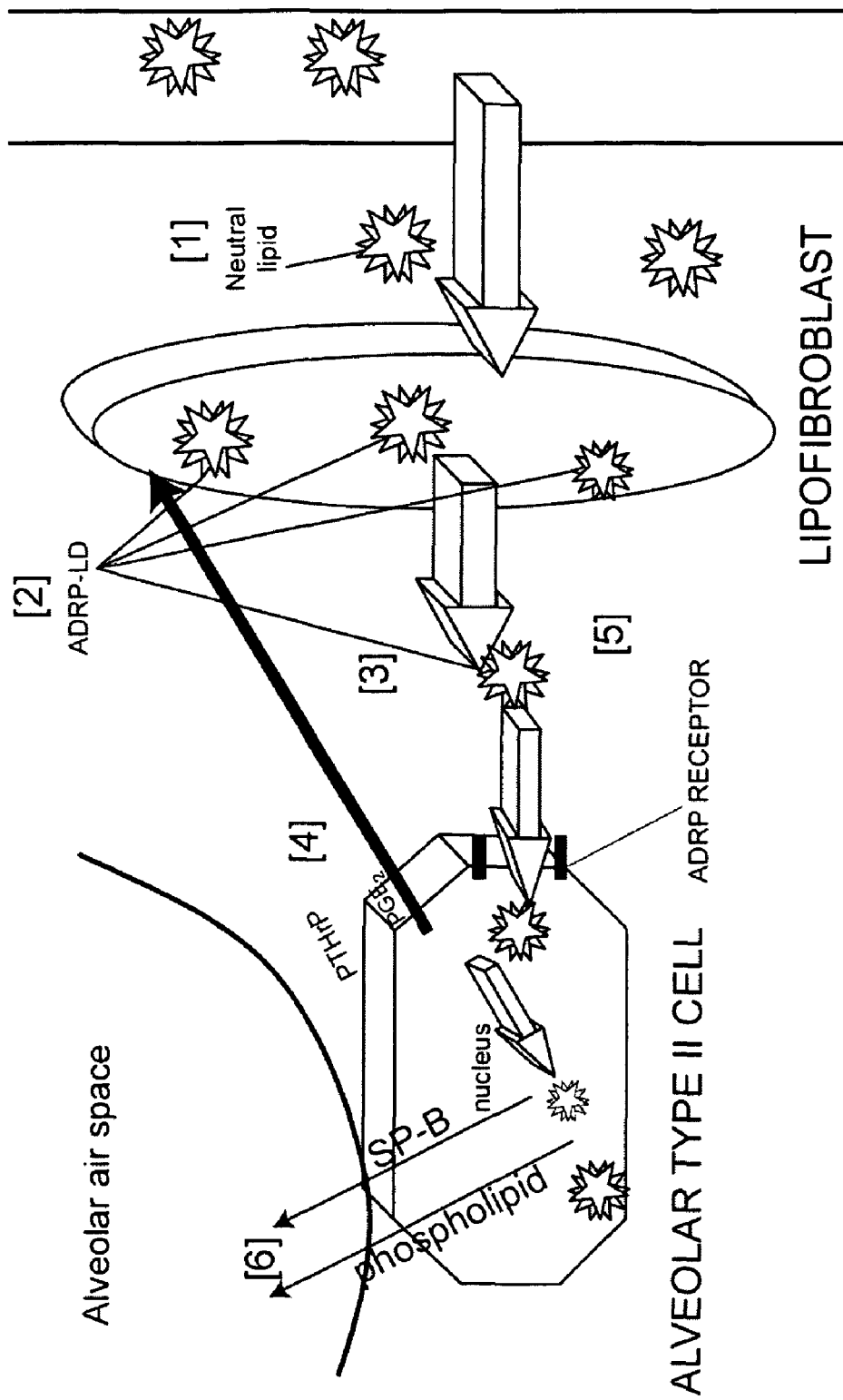
FIG. 9 illustrates a schematic for the lipid trafficking mechanism for coordinate regulation of surfactant protein and phospholipid synthesis, which depicts (1) the active recruitment of circulating lipid by the lipofibroblast, (2) the formation of ADRP-lipid droplets by the lipofibroblast, (3) active ADRP-LD secretion (4) in response to stretch-regulated, alveolar type II cell-produced PTHrP and prostaglandin $E_2$ (PGE$_2$), (5) ADRP-LD uptake by alveolar type II cells via a receptor-mediated mechanism, and (6) coordinate regulation of surfactant phospholipid and SP-B, resulting in simultaneous increases in surfactant protein and phospholipid production by the alveolar type II cell.

In conclusion, we provide a Schematic (FIG. 9) for this lipid trafficking mechanism which depicts (1) the active recruitment of circulating lipid by the LIF, (2) the formation of ADRP-lipid droplets by the LIF, (3) stimulation of ADRP-LD synthesis and secretion (4) in response to ATII-produced ADRP and prostaglandin $E_2$ ($PGE_2$), respectively, (5) ADRP-LD uptake by AIIs via a receptor-mediated mechanism, and (6) coordinate stimulation of surfactant phospholipid and SP-B, resulting in simultaneous increases in surfactant protein and phospholipid production by the ATII cell.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A chimeric moiety comprising a full length adipocyte differentiation-related protein (ADRP) or an ADRP fragment comprising at least 300 amino acids of the carboxyl terminal of ADRP, wherein said full length protein or ADRP fragment is covalently coupled to a liposome containing a drug or a lipid complexed with a drug, wherein said drug is an anticancer drug, and wherein said ADRP or ADRP fragment is disposed on said liposome or lipid to permit binding of the ADRP or ADRP fragment to an ADRP receptor.

2. The chimeric moiety of claim 1, wherein said ADRP is a full length ADRP.

3. The chimeric moiety of claim 1, wherein said ADRP is a carboxyl terminal fragment of ADRP of at least 300 amino acids and of sufficient length to induce transport of said lipid or liposome into an epithelial cell.

4. The chimeric moiety of claim 1, wherein said lipid or liposome is a neutral lipid or a liposome formed of neutral lipids.

5. The chimeric moiety of claim 1, wherein said lipid or liposome is a neutral lipid or a liposome comprising triacylglycerol.

6. The chimeric moiety of claim 1, wherein said lipid or liposome is a multilamellar liposome.

7. The chimeric moiety of claim 1, wherein said lipid or liposome is a unilamellar liposome.

8. The chimeric moiety of claim 1, wherein said lipid or liposome is a lipid.

9. The chimeric moiety of claim 1, wherein said lipid or liposome is a liposome.

10. The chimeric moiety of claim 8 or 9, wherein said drug comprises a retinoid.

11. The chimeric moiety of claim 8 or 9, wherein said drug is selected from the group consisting of retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol.

* * * * *